(12) United States Patent
Tajima et al.

(10) Patent No.: US 7,906,511 B2
(45) Date of Patent: Mar. 15, 2011

(54) CYCLIC COMPOUND HAVING PYRIMIDINYLALKYLTHIO GROUP

(75) Inventors: Hisashi Tajima, Ikoma (JP); Takahiro Honda, Ikoma (JP); Kenji Kawashima, Ikoma (JP); Kazuyoshi Okamoto, Ikoma (JP); Minoru Yamamoto, Ikoma (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 729 days.

(21) Appl. No.: 11/887,308

(22) PCT Filed: Mar. 31, 2006

(86) PCT No.: PCT/JP2006/306825
§ 371 (c)(1),
(2), (4) Date: Sep. 27, 2007

(87) PCT Pub. No.: WO2006/106914
PCT Pub. Date: Oct. 12, 2006

(65) Prior Publication Data
US 2009/0291951 A1    Nov. 26, 2009

(30) Foreign Application Priority Data
Mar. 31, 2005   (JP) .................. 2005-101994

(51) Int. Cl.
C07D 239/42 (2006.01)
C07D 401/12 (2006.01)
C07D 401/14 (2006.01)
A61K 31/506 (2006.01)
A61K 31/5377 (2006.01)

(52) U.S. Cl. ........... 514/235.8; 514/252.14; 514/252.18; 514/275; 544/122; 544/295; 544/316; 544/318; 544/331; 544/332

(58) Field of Classification Search .................. 544/122, 544/295, 316, 318, 331, 332; 514/235.8, 514/252.14, 252.18, 275
See application file for complete search history.

(56) References Cited

U.S. PATENT DOCUMENTS
2003/0073845 A1   4/2003   Barta et al.
2003/0171404 A1   9/2003   Barta et al.

FOREIGN PATENT DOCUMENTS
| WO | WO 97/30035 A1 | 8/1997 |
| WO | WO 98/35958 A1 | 8/1998 |
| WO | WO 98/50356 A1 | 11/1998 |
| WO | WO 00/27819 A1 | 5/2000 |
| WO | WO 01/55114 A1 | 8/2001 |
| WO | WO 02/066470 A1 | 8/2002 |
| WO | WO 03/007930 A2 | 1/2003 |
| WO | WO 03/007954 A2 | 1/2003 |
| WO | WO 03/016306 A1 | 2/2003 |
| WO | WO 2004/005279 A2 | 1/2004 |
| WO | WO 2004/078723 A1 | 9/2004 |
| WO | WO 2005/085201 A1 | 9/2005 |

OTHER PUBLICATIONS

Fabbro et al., Protein kinases as targets for anticancer agents: from inhibitors to useful drugs, Pharmacology & Therapeutics, 93, pp. 79-98, 2002.*
Traxler, Protein tyrosine kinase inhibitors in cancer treatment, Exp. Opin. Ther. Patents, 7(6), pp. 571-588, 1997.*
Simone, Oncology: Introduction, 20th Edition, vol. 1, pp. 1004-1010, 1996.*
Cressey et al., Medline Abstract (BMC Cancer, vol. 5, p. 128) Oct. 2005.*
Yano et al., Medline Abstract (Clinical Cancer Research: An Official Journal of the American Association for Cancer Research, vol. 6, Issue 3, pp. 957-965) Mar. 2000.*
Molecular Medicine, vol. 35, special issue, "Molecular Mechanism of Symptoms and Pathologic Conditions," Nakayama Shoten, 73-74 (1998).
Protein, Nucleic Acid, Enzyme, extra number, "The Most Advanced Development of New Drugs," Kyoritsu Shuppan, 1182-1187 (2000).

* cited by examiner

Primary Examiner — Deepak Rao
(74) Attorney, Agent, or Firm — Holtz, Holz, Goodman and Chick PC

(57) ABSTRACT

The present invention has its object to study synthesis of novel cyclic compounds having a pyrimidinylalkylthio group and to find pharmacological actions of the compounds. According to the present invention, a compound represented by the formula (1) or a salt thereof is provided.

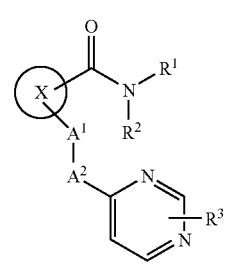

(1)

In the formula, the ring X represents:

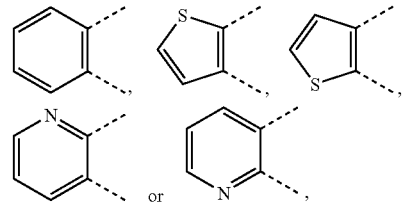

$R^1$ and $R^2$ independently represent a hydrogen atom, an alkyl group, an aryl group, an aromatic heterocyclic group or the like; $R^3$ represents a hydrogen atom, a halogen atom, a hydroxy group, an alkoxy group, an aryloxy group, an alkyl group, an aryl group, an amino group, an alkylamino group or the like; $A^1$ represents a sulfur atom or the like; and $A^2$ represents an alkylene group.

6 Claims, No Drawings

CYCLIC COMPOUND HAVING PYRIMIDINYLALKYLTHIO GROUP

This application is the United States national phase application of International Application PCT/JP2006/306825 filed Mar. 31, 2006.

TECHNICAL FIELD

The present invention relates to a novel cyclic compound having a pyrimidinylalkylthio group or a salt thereof useful as a pharmaceutical. Such a compound is useful as a therapeutic agent for a disease associated with angiogenesis, particularly as a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

BACKGROUND ART

Angiogenesis is a phenomenon in which a new vascular network is formed from an existing blood vessel and is observed mainly in a microvessel. Angiogenesis is originally a physiological phenomenon and is essential for blood vessel formation in fetal life, but it is usually observed only at a limited site such as endometrium or follicle or at a limited period such as a wound healing process in adults. However, pathological angiogenesis is observed in a disease such as cancer, rheumatoid arthritis, age-related macular degeneration, diabetic retinopathy, retinopathy of prematurity, retinal vein occlusion, polypoid choroidal angiopathy, diabetic macular edema, psoriasis vulgaris or atherosclerosis, and closely relates to the progress of pathological conditions of these diseases. It is considered that angiogenesis is regulated by balance between its promoting factor and inhibitory factor, and angiogenesis is caused by disruption of the balance (see Molecular Medicine vol. 35, special issue, "Molecular Mechanism of Symptoms and Pathological conditions", Nakayama Syoten, 73-74 (1998) and Protein, Nucleic Acid, Enzyme and extra number, "The Most Advanced Development of New Drugs", Kyoritsu Shuppan, 1182-1187 (2000)).

A vascular endothelial growth factor (hereinafter abbreviated as "VEGF") is a factor which specifically acts on a receptor (Flt-1, KDR/Flk-1 or the like) present on the surface of vascular endothelial cells, thereby to promote proliferation and migration of the vascular endothelial cells, construction of a capillary vessel network due to vasculogenesis, and plays a very important role in incidence of angiogenesis. Accordingly, there have been many reports on attempts to treat a disease associated with angiogenesis by inhibiting VEGF to control the incidence of angiogenesis. Examples of drugs to be used for the treatment include indolin-2-one derivatives (see WO 98/50356), phthalazine derivatives (see WO 98/35958), quinazoline derivatives (see WO 97/30035), anthranilic acid amide derivatives (see WO 00/27819), 2-aminonicotinic acid derivatives (see WO 01/55114), 4-pyridylalkylthio derivatives (see WO 04/078723) and the like.

However, there is no description on cyclic compounds having a pyrimidinylalkylthio group in these patent publications.

On the other hand, cyclic compounds having a pyrimidinylalkylthio group is reported in WO 03/016306. This patent publication relates to pyrimidine derivatives having an HIV inhibitory activity, however, this patent publication only discloses enormous combinations of chemical structures and does not make specific disclosure of cyclic compounds having a pyrimidinylalkylthio group according to the present invention at all.

DISCLOSURE OF THE INVENTION

Problems to be Solved

It is a very interesting subject to study synthesis of novel cyclic compounds having a pyrimidinylalkylthio group and to find pharmacological actions of the compounds.

Means of Solving Problems

The present inventors have studied synthesis of cyclic compounds having a pyrimidinylalkylthio group and succeeded in producing a large number of novel compounds.

Further, they studied pharmacological actions of these compounds widely, and found that these compounds have an antiangiogenic effect, and are useful as a therapeutic agent for a disease associated with angiogenesis, particularly as a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like, thus accomplished the present invention.

Advantage of the Invention

The present invention provides a novel cyclic compound having a pyrimidinylalkylthio group or a salt thereof useful as a pharmaceutical. The novel cyclic compound according to the present invention has an excellent antiangiogenic effect, and is useful as a therapeutic agent for a disease associated with angiogenesis, for example, cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

BEST MODE FOR CARRYING OUT THE INVENTION

The present invention relates to a compound represented by the general formula (1) or a salt thereof (hereinafter referred to as "the compound of the present invention" unless otherwise specified) and a pharmaceutical composition containing the compound of the present invention. Describing a pharmaceutical use of the compound of the present invention more specifically, it relates to a therapeutic agent for a disease associated with angiogenesis containing the compound of the present invention as an active ingredient, and for example, it relates to a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis, vulgaris, atherosclerosis or the like.

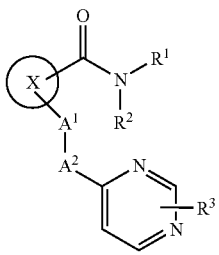

(1)

[In the formula, the ring X represents:

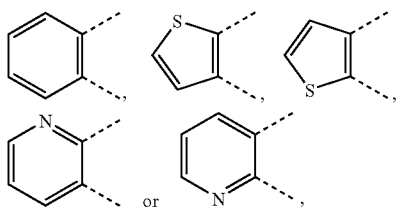

which may have one or plural substituents selected from a halogen atom and an alkyl group;

$R^1$ and $R^2$ may be the same or different and each represents a hydrogen atom, an alkyl group, an aryl group or an aromatic heterocyclic group;

in the case where $R^1$ or $R^2$ is an alkyl group, the alkyl group may have one or plural substituents selected from an aryl group, a halogenoaryl group, an alkoxyaryl group and an alkylaryl group;

in the case where $R^1$ or $R^2$ is an aryl group, the aryl group may have one or plural substituents selected from a halogen atom, a hydroxy group, an alkoxy group, a halogenoalkoxy group, an alkyl group, a halogenoalkyl group, an aryl group, a halogenoaryl group, an alkoxyaryl group and an alkylaryl group;

$R^1$ and $R^2$ may be combined together to form a nonaromatic heterocycle;

$R^3$ represents a hydrogen atom, a halogen atom, a hydroxy group, an alkoxy group, an aryloxy group, an alkyl group, an aryl group, an amino group, an alkylamino group, a cycloalkylamino group, an arylamino group, an alkylcarbonylamino group, an arylcarbonylamino group, a mercapto group, an alkylthio group, an arylthio group, an alkylsulfinyl group or a nonaromatic heterocyclic group;

in the case where $R^3$ is an alkylamino group or an alkylcarbonylamino group, the alkyl moiety of which may have one or plural substituents selected from a hydroxy group, an alkoxy group, an aryl group, an amino group, an alkylamino group and a nonaromatic heterocyclic group;

in the case where $R^3$ is a cycloalkylamino group, the cycloalkyl moiety of which may have one or plural substituents selected from a hydroxy group and an alkoxy group;

in the case where $R^3$ is a nonaromatic heterocyclic group, the ring of which may have one or plural substituents selected from an alkyl group, a hydroxyalkyl group and an alkoxyalkyl group;

$A^1$ represents a sulfur atom, a sulfinyl group or a sulfonyl group; and $A^2$ represents an alkylene group.

Hereinafter the same definition shall apply.]

The respective atoms and groups as used in the claims and specification have the following meanings throughout the claims and specification.

The "halogen atom" refers to fluorine, chlorine, bromine or iodine.

The "alkyl" refers to straight-chain or branched alkyl having 1 to 6 carbon atoms. Specific examples thereof include methyl, ethyl, n-propyl, n-butyl, n-pentyl, n-hexyl, isopropyl, isobutyl, sec-butyl, tert-butyl, isopentyl and the like.

The "cycloalkyl" refers to cycloalkyl having 3 to 8 carbon atoms. Specific examples thereof include cyclopropyl, cyclobutyl, cyclopentyl, cyclohexyl, cycloheptyl, cyclooctyl and the like.

The "aryl" refers to monocyclic aromatic hydrocarbon, or bicyclic or tricyclic condensed polycyclic aromatic hydrocarbon having 6 to 14 carbon atoms. Further, condensed polycyclic hydrocarbon formed by condensation of such monocyclic aromatic hydrocarbon, or bicyclic or tricyclic condensed polycyclic aromatic hydrocarbon with a cycloalkane ring is also included in the "aryl" of the present invention. Specific examples of the monocyclic aromatic hydrocarbon include phenyl, and specific examples of the condensed polycyclic aromatic hydrocarbon include naphthyl, anthryl, phenanthryl and the like, and specific examples of the condensed polycyclic hydrocarbon include indanyl, tetrahydronaphthyl, tetrahydroanthryl and the like.

The "aromatic heterocycle" refers to a monocyclic aromatic heterocycle, or a bicyclic or tricyclic condensed polycyclic aromatic heterocycle having one or plural heteroatoms (a nitrogen atom, an oxygen atom or a sulfur atom) in the ring.

Specific examples of the monocyclic aromatic heterocycle include aromatic heterocycles having one heteroatom in the ring such as pyrrole, furan, thiophene and pyridine; azole aromatic heterocycles such as imidazole, oxazole, thiazole, pyrazole, isoxazole and isothiazole; aromatic heterocycles having two nitrogen atoms in the ring such as pyrazine and pyrimidine and the like. Specific examples of the bicyclic or tricyclic condensed polycyclic aromatic heterocycle include condensed aromatic heterocycles such as indole, isoindole, benzoimidazole, benzoxazole, benzothiazole, quinoline, isoquinoline, thianthrene, phenoxathiin and phenanthroline and the like.

The "nonaromatic heterocycle" refers to a monocyclic nonaromatic heterocycle, or a bicyclic or tricyclic condensed polycyclic nonaromatic heterocycle having one or plural heteroatoms (a nitrogen atom, an oxygen atom or a sulfur atom) in the ring.

Specific examples of the monocyclic nonaromatic heterocycle include saturated nonaromatic heterocycles having one heteroatom in the ring such as pyrrolidine, tetrahydrofuran, tetrahydrothiophene, piperidine, tetrahydropyran and homopiperazine; saturated nonaromatic heterocycles having two heteroatoms in the ring such as imidazolidine, oxazolidine, thiazolidine, pyrazolidine, piperazine, morpholine, thiomorpholine, homopiperidine and homomorpholine; unsaturated nonaromatic heterocycles having one heteroatom in the ring such as pyrroline, dihydrofuran, dihydrothiophene, tetrahydropyridine, dihydropyridine, dihydropyran and pyran; unsaturated nonaromatic heterocycles having two heteroatoms such as imidazoline, oxazoline, thiazoline and pyrazoline, and the like. Specific examples of the bicyclic or tricyclic condensed polycyclic nonaromatic heterocycle include chromane, indoline, isoindoline, xanthine and the like.

The "alkoxy" refers to straight-chain or branched alkoxy having 1 to 6 carbon atoms. Specific examples thereof include methoxy, ethoxy, n-propoxy, n-butoxy, n-pentoxy, n-hexyloxy, isopropoxy, isobutoxy, sec-butoxy, tert-butoxy, isopentoxy and the like.

The "aryloxy" refers to monocyclic aromatic hydrocarbonoxy, or bicyclic or tricyclic condensed polycyclic aromatic hydrocarbonoxy having 6 to 14 carbon atoms. Specific examples of the monocyclic aromatic hydrocarbonoxy include phenoxy, and specific examples of the condensed polycyclic aromatic hydrocarbonoxy include naphthyloxy, anthryloxy, phenanthryloxy and the like.

The "alkylamino" refers to monoalkylamino having 1 to 6 carbon atoms or dialkylamino having 2 to 12 carbon atoms. Specific examples of the monoalkylamino include methylamino, ethylamino, hexylamino and the like, and specific examples of the dialkylamino include ethylmethylamino, dimethylamino, diethylamino, dihexylamino and the like.

The "cycloalkylamino" refers to monocycloalkylamino having 3 to 22 carbon atoms or dicycloalkylamino having 6 to 16 carbon atoms. Specific examples of the monocycloalkylamino include cyclopropylamino, cyclobutylamino, cyclohexylamino, cyclopropylphenylamino and the like, and specific examples of the dicycloalkylamino include dicyclopropylamino, dicyclobutylamino, dicyclopentylamino, dicyclohexylamino, dicycloheptylamino, dicyclooctylamino and the like.

The "arylamino" refers to monoarylamino having 6 to 20 carbon atoms or diarylamino having 12 to 28 carbon atoms. Specific examples of the monoarylamino include phenylamino, naphthylamino, ethylphenylamino and the like, and specific examples of the diarylamino include diphenylamino, dianthrylamino and the like.

The "alkylcarbonylamino" refers to monoalkylcarbonylamino having 2 to 7 carbon atoms or dialkylcarbonylamino having 4 to 14 carbon atoms. Specific examples of the monoalkylcarbonylamino include methylcarbonylamino, ethylcarbonylamino, hexylcarbonylamino and the like, and specific examples of the dialkylcarbonylamino include ethylmethylcarbonylamino, dimethylcarbonylamino, diethylcarbonylamino, dihexylcarbonylamino and the like.

The "arylcarbonylamino" refers to monoarylcarbonylamino having 7 to 21 carbon atoms or diarylcarbonylamino having 14 to 30 carbon atoms. Specific examples of the monoarylcarbonylamino include phenylcarbonylamino, naphthylcarbonylamino, ethylphenylcarbonylamino and the like, and specific examples of the diarylcarbonylamino include diphenylcarbonylamino, dianthrylcarbonylamino and the like.

The "alkylthio" refers to straight-chain or branched alkylthio having 1 to 6 carbon atoms. Specific examples thereof include methylthio, ethylthio, n-propylthio, n-butylthio, n-pentylthio, n-hexylthio, isopropylthio, isobutylthio, sec-butylthio, tert-butylthio, isopentylthio and the like.

The "arylthio" refers to monocyclic aromatic hydrocarbonthio, or bicyclic or tricyclic condensed polycyclic aromatic hydrocarbonthio having 6 to 14 carbon atoms. Specific examples of the monocyclic aromatic hydrocarbonthio include phenylthio, and specific examples of the condensed polycyclic aromatic hydrocarbonthio include naphthylthio, anthrylthio, phenanthrylthio and the like.

The "alkylsulfinyl" refers to straight-chain or branched alkylsulfinyl having 1 to 6 carbon atoms. Specific examples thereof include methylsulfinyl, ethylsulfinyl, n-propylsulfinyl, n-butylsulfinyl, n-pentylsulfinyl, n-hexylsulfinyl, isopropylsulfinyl, isobutylsulfinyl, sec-butylsulfinyl, tert-butylsulfinyl, isopentylsulfinyl and the like.

The "alkylene" refers to straight-chain or branched alkylene having 1 to 6 carbon atoms. Specific examples thereof include methylene, ethylene, trimethylene, tetramethylene, pentamethylene, hexamethylene, methylmethylene, dimethylmethylene, propylene, 2-methyltrimethylene and the like.

The "halogenoalkoxy" refers to alkoxy having one or plural of the same or different halogen atoms as substituents.

The "halogenoalkyl" refers to alkyl having one or plural of the same or different halogen atoms as substituents.

The "halogenoaryl" refers to aryl having one or plural of the same or different halogen atoms as substituents.

The "alkoxyaryl" refers to aryl having one or plural of the same or different alkoxy groups as substituents.

The "alkylaryl" refers to aryl having one or plural of the same or different alkyl groups as substituents.

When the compound of the present invention has a free hydroxy group, amino group, alkylamino group, cycloalkylamino group, arylamino group, alkylcarbonylamino group, arylcarbonylamino group or mercapto group as a substituent, these substituents may be protected with a protecting group. Further, when the aromatic heterocyclic group or the nonaromatic heterocycle has a free nitrogen atom, the nitrogen atom may also be protected with a protecting group.

The "protecting group for a free hydroxy group" refers to a group widely used as a protecting group for a free hydroxy group including a substituted or unsubstituted alkyl group, or an unsubstituted alkenyl group such as a methyl group, a methoxymethyl group, a benzyl group, a 4-methoxyphenylmethyl group or an allyl group; a substituted or unsubstituted nonaromatic heterocyclic group such as a 3-bromotetrahydropyranyl group, a tetrahydropyranyl group or a tetrahydrofuranyl group; a substituted or unsubstituted alkylcarbonyl group or a substituted or unsubstituted arylcarbonyl group such as an acetyl group, a trifluoroacetyl group, a benzoyl group or a 4-chlorobenzoyl group; a substituted or unsubstituted alkyloxycarbonyl group, an unsubstituted alkenyloxycarbonyl group, or a substituted or unsubstituted aryloxycarbonyl group such as a methoxycarbonyl group, an ethoxycarbonyl group, an isobutoxycarbonyl group, a tert-butoxycarbonyl group, a benzyloxycarbonyl group, a p-methoxybenzyloxycarbonyl group, a 9-fluorenylmethoxycarbonyl group, a vinyloxycarbonyl group, an aryloxycarbonyl group, a phenyloxycarbonyl group or a p-nitrophenyloxycarbonyl group; a substituted silyl group such as a trimethylsilyl group, a triethylsilyl group, a triisopropylsilyl group, a tert-butyldimethylsilyl group or a tert-butyldiphenylsilyl group, and the like.

The "protecting group for a free amino group, a free alkylamino group, a free cycloalkylamino group, a free arylamino group, a free alkylcarbonylamino group, a free arylcarbonylamino group, an aromatic heterocyclic group having a free nitrogen atom, or a nonaromatic heterocyclic group having a free nitrogen atom" refers to a group widely used as a protecting group for a free amino group, a free alkylamino group, a free cycloalkylamino group, a free arylamino group, a free alkylcarbonylamino group, a free arylcarbonylamino group, an aromatic heterocyclic group having a free nitrogen atom, or a nonaromatic heterocyclic group having a free nitrogen atom including an unsubstituted alkenyl group such as an allyl group; a hydrocarbonyl group such as a formyl group; a substituted or unsubstituted alkylcarbonyl group, a substituted or unsubstituted arylcarbonyl group, or an unsubstituted aromatic heterocyclic carbonyl group such as an acetyl group, a trichloroacetyl group, a trifluoroacetyl group, a benzoyl group, a 4-chlorobenzoyl group or a picolinoyl group; a substituted or unsubstituted alkyloxycarbonyl group, or a substituted or unsubstituted aryloxycarbonyl group such as a methoxycarbonyl group, an isobutoxycarbonyl group, a tert-butoxycarbonyl group, a 2,2,2-trichloroethoxycarbonyl group, a benzyloxycarbonyl group, a diphenylmethoxycarbonyl group, a phenoxycarbonyl group or a m-nitrophenoxycarbonyl group; a substituted or unsubstituted alkylsulfonyl group, or a substituted or unsubstituted arylsulfonyl group such as a methylsulfonyl group, a benzylsulfonyl group, a phenylsulfonyl group, a 4-chlorophenylsulfonyl group, a tolylsulfonyl group or a 2,4,6-trimethylphenylsulfonyl group, and the like.

The "protecting group for a free mercapto group" refers to a group widely used as a protecting group for a free mercapto group including a substituted or unsubstituted alkyl group, or an unsubstituted alkenyl group such as a methyl group, a methoxymethyl group, a benzyl group, a 4-methoxyphenylmethyl group or an allyl group; a substituted or unsubstituted nonaromatic heterocyclic group such as a 3-bromotetrahydropyranyl group, a tetrahydropyranyl group or a tetrahydrofuranyl group; a substituted or unsubstituted alkylcarbonyl group, or a substituted or unsubstituted arylcarbonyl group such as an acetyl group, a trifluoroacetyl group, a benzoyl group or a 4-chlorobenzoyl group; a substituted or unsubstituted alkyloxycarbonyl group, an unsubstituted alkenyloxycarbonyl group, or a substituted or unsubstituted aryloxycarbonyl group such as a methoxycarbonyl group, an ethoxycarbonyl group, an isobutoxycarbonyl group, a tert-butoxycarbonyl group, a benzyloxycarbonyl group, a p-methoxybenzyloxycarbonyl group, a 9-fluorenylmethoxycarbonyl group, a vinyloxycarbonyl group, an aryloxycarbonyl group, a phenyloxycarbonyl group or a p-nitrophenyloxycarbonyl group, and the like.

The above-mentioned substituted alkyl group, substituted nonaromatic heterocyclic group, substituted alkylcarbonyl group, substituted arylcarbonyl group, substituted alkyloxycarbonyl group, substituted aryloxycarbonyl group, substituted silyl group, substituted alkylsulfonyl group and substituted arylsulfonyl group refer to an alkyl group, a nonaromatic heterocyclic group, an alkylcarbonyl group, an arylcarbonyl group, an alkyloxycarbonyl group, an aryloxycarbonyl group, a silyl group, an alkylsulfonyl group and an arylsulfonyl group substituted with one or plural groups selected from a halogen atom, an alkoxy group, an alkyl group, an aryl group, a halogenoaryl group, an alkoxyaryl group and a nitro group, respectively.

The "plural groups" as used herein may be the same or different from one another and refer to preferably 2 or 3 groups, and more preferably 2 groups.

Further, in the "group" as used herein, a hydrogen atom and a halogen atom are also included.

The "salt" of the compound of the present invention is not particularly limited as long as it is a pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumalic acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid or sulfosalicylic acid; quaternary ammonium salts with methyl bromide, methyl iodide or the like; salts with a halogen ion such as a bromine ion, a chlorine ion or an iodine ion; salts with an alkali metal such as lithium, sodium or potassium; salts with an alkaline earth metal such as calcium or magnesium; salts with a metal such as iron or zinc; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine or N,N-bis(phenylmethyl)-1,2-ethanediamine, and the like.

In the case where there are geometrical isomers or optical isomers in the compound of the present invention, these isomers are also included in the scope of the present invention.

Further, the compound of the present invention may be in the form of a hydrate or a solvate.

Further, in the case where there is proton tautomerism in the compound of the present invention, the tautomeric isomers thereof are also included in the scope of the present invention.

(a) Preferred examples of the compound of the present invention include compounds in which the respective groups are as defined below in the compounds represented by the general formula (1) and salts thereof.

In the general formula (1), (a1) The ring X represents:

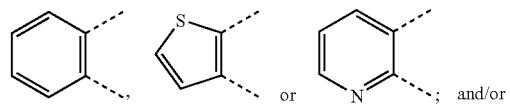

(a2) $R^1$ represents an aryl group or an aromatic heterocyclic group; and/or (a3) in the case where $R^1$ is an aryl group, the aryl group may have one or plural substituents selected from a halogen atom, a hydroxy group, an alkoxy group, a halogenoalkoxy group, an alkyl group, a halogenoalkyl group and an aryl group; and/or (a4) $R^2$ represents a hydrogen atom; and/or (a5) $R^3$ represents a hydrogen atom, an amino group, an alkylamino group, a cycloalkylamino group, an arylamino group, an alkylcarbonylamino group, a mercapto group, an alkylthio group, an arylthio group, an alkylsulfinyl group or a nonaromatic heterocyclic group; and/or (a6) in the case where $R^3$ is an alkylamino group, the alkyl moiety of which may have one or plural substituents selected from a hydroxy group, an alkoxy group, an aryl group and a nonaromatic heterocyclic group; and/or (a7) in the case where $R^3$ is a cycloalkylamino group, the cycloalkyl moiety of which may have one or plural substituents selected from a hydroxy group and an alkoxy group; and/or (a8) in the case where $R^3$ is a nonaromatic heterocyclic group, the ring of which may have one or plural substituents selected from an alkyl group, a hydroxyalkyl group and an alkoxyalkyl group; and/or (a9) $A^1$ represents a sulfur atom; and/or (a10) $A^2$ represents an alkylene group.

That is, in the compounds represented by the general formula (1), preferred examples include compounds that comprise one or a combination of two or more selected from the above (a1), (a2), (a3), (a4), (a5), (a6), (a7), (a8), (a9) and (a10) and salts thereof.

(b) More preferred examples of the compound of the present invention include compounds in which the respective groups are as defined below in the compounds represented by the general formula (1) and salts thereof.

(b1) The ring X represents:

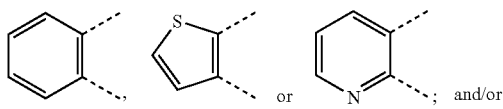
or   ; and/or (b2) R¹ represents an aryl group or an aromatic heterocyclic group; and/or (b3) in the case where R¹ is an aryl group, the aryl group may have one or plural substituents selected from a halogen atom, an alkoxy group, a halogenoalkoxy group, an alkyl group and a halogenoalkyl group; and/or (b4) R² represents a hydrogen atom; and/or (b5) R³ represents a hydrogen atom, an amino group, an alkylamino group, a cycloalkylamino group, an alkylcarbonylamino group, an alkylthio group, or a nonaromatic heterocyclic group; and/or (b6) in the case where R³ is an alkylamino group, the alkyl moiety of which may have one or plural substituents selected from a hydroxy group, an alkoxy group, an aryl group and a nonaromatic heterocyclic group; and/or (b7) in the case where R³ is a cycloalkylamino group, the cycloalkyl moiety of which may have one or plural hydroxy groups as substituents; and/or (b8) in the case where R³ is a nonaromatic heterocyclic group, the ring of which may have one or plural substituents selected from an alkyl group and a hydroxyalkyl group; and/or (b9) A¹ represents a sulfur atom; and/or (b10) A² represents an alkylene group.

That is, in the compounds represented by the general formula (1), more preferred examples include compounds that comprise one or a combination of two or more selected from the above (b1), (b2), (b3), (b4), (b5), (b6), (b7), (b8), (b9) and (b10) and salts thereof.

(c) Particularly preferred examples of the compound of the present invention include compounds in which the respective groups are as defined below in the compounds represented by the general formula (1) and salts thereof.

(c1) The ring X represents:

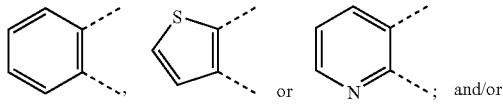
or   ; and/or (c2) R¹ represents a phenyl group, a 3-chlorophenyl group, a 4-chlorophenyl group, a 4-methoxyphenyl group, a 4-trifluoromethoxyphenyl group, a 4-n-propylphenyl group, a 3-isopropylphenyl group, a 4-tert-butylphenyl group, a 3-trifluoromethylphenyl group, a 5-chloro-2,4-dimethoxyphenyl group, a 3,5-dimethylphenyl group, an indan-5-yl group, a 1H-indazol-6-yl group, a quinoline-6-yl group or an isoquinoline-3-yl group; and/or (c3) R² represents a hydrogen atom; and/or (c4) R³ represents a hydrogen atom, an amino group, a methylamino group, an n-butylamino group, a dimethylamino group, a 2-hydroxyethylamino group, a 2-ethoxyethylamino group, a 1-phenylethylamino group, a 2-morpholinoethylamino group, a cyclopropylamino group, a cyclobutylamino group, a 4-hydroxycyclohexylamino group, an acetylamino group, a diacetylamino group, a methylthio group, a morpholino group, a piperazinyl group, a 4-methylpiperazinyl group or a 4-(2-hydroxyethyl)piperazinyl group; and/or (c5) A¹ represents a sulfur atom; and/or (c6) A² represents a methylene group.

That is, in the compounds represented by the general formula (1), particularly preferred examples include compounds that comprise one or a combination of two or more selected from the above (c1), (c2), (c3), (c4), (c5) and (c6), and salts thereof.

(d) Particularly preferred specific examples of the compound of the present invention include compounds described below and salts thereof.

2-(2-Aminopyrimidin-4-ylmethylthio)-N-(3,5-dimethylphenyl)pyridine-3-carboxamide 2-(2-Aminopyrimidin-4-ylmethylthio)-N-(4-chlorophenyl)pyridine-3-carboxamide 2-(2-Aminopyrimidin-4-ylmethylthio)-N-(4-trifluoromethoxyphenyl)pyridine-3-carboxamide 2-(2-Aminopyrimidin-4-ylmethylthio)-N-(3-isopropylphenyl)pyridine-3-carboxamide 2-(2-Aminopyrimidin-4-ylmethylthio)-N-(quinolin-6-yl)pyridine-3-carboxamide 2-(2-Aminopyrimidin-4-ylmethylthio)-N-(isoquinolin-3-yl)pyridine-3-carboxamide 2-(2-Aminopyrimidin-4-ylmethylthio)-N-(3,5-dimethylphenyl)benzamide 2-(2-Aminopyrimidin-4-ylmethylthio)-N-(4-chlorophenyl)benzamide 3-(2-Aminopyrimidin-4-ylmethylthio)-N-(3,5-dimethylphenyl)thiophene-2-carboxamide N-(3,5-Dimethylphenyl)-2-(pyrimidin-4-ylmethylthio)pyridine-3-carboxamide N-(4-Chlorophenyl)-2-(pyrimidin-4-ylmethylthio)pyridine-3-carboxamide N-(3,5-Dimethylphenyl)-2-(2-methylthiopyrimidin-4-ylmethylthio)pyridine-3-carboxamide N-(3,5-Dimethylphenyl)-2-(2-methylaminopyrimidin-4-ylmethylthio)pyridine-3-carboxamide 2-(2-Dimethylaminopyrimidin-4-ylmethylthio)-N-(3,5-dimethylphenyl)pyridine-3-carboxamide 2-(2-Acetylaminopyrimidin-4-ylmethylthio)-N-(3,5-dimethylphenyl)pyridine-3-carboxamide 2-(2-Acetylaminopyrimidin-4-ylmethylthio)-N-(4-chlorophenyl)pyridine-3-carboxamide 2-(2-Acetylaminopyrimidin-4-ylmethylthio)-N-(4-trifluoromethoxyphenyl)pyridine-3-carboxamide 2-(2-Acetylaminopyrimidin-4-ylmethylthio)-N-(indan-5-yl)pyridine-3-carboxamide 2-(2-Diacetylaminopyrimidin-4-ylmethylthio)-N-(3,5-dimethylphenyl)pyridine-3-carboxamide 2-(2-Cyclopropylaminopyrimidin-4-ylmethylthio)-N-(3,5-dimethylphenyl)pyridine-3-carboxamide N-(4-Chlorophenyl)-2-(2-morpholinopyrimidin-4-ylmethylthio)pyridine-3-carboxamide 2-(2-Morpholinopyrimidin-4-ylmethylthio)-N-(4-trifluoromethoxyphenyl)pyridine-3-carboxamide N-(3,5-Dimethylphenyl)-2-(2-morpholinopyrimidin-4-ylmethylthio)pyridine-3-carboxamide N-(4-Chlorophenyl)-2-(2-cyclopropylaminopyrimidin-4-ylmethylthio)pyridine-3-carboxamide 2-(2-Cyclopropylaminopyrimidin-4-ylmethylthio)-N-(4-trifluoromethoxyphenyl)pyridine-3-carboxamide 2-(2-Cyclopropylaminopyrimidin-4-ylmethylthio)-N-(3-trifluoromethylphenyl)pyridine-3-carboxamide 2-(2-n-Butylaminopyrimidin-4-ylmethylthio)-N-(3,5-dimethylphenyl)pyridine-3-carboxamide 2-[2-(4-Acetylpiperazin-1-yl)pyrimidin-4-ylmethylthio]-N-(3,5-dimethylphenyl)pyridine-3-carboxamide N-(3,5-Dimethylphenyl)-2-[2-(2-hydroxyethyl)aminopyrimidin-4-ylmethylthio]pyridine-3-carboxamide 2-[2-(2-Ethoxyethyl)aminopyrimidin-4-ylmethylthio]-N-(4-trifluoromethoxyphenyl)pyridine-3-carboxamide N-(4-Chlorophenyl)-2-(pyrimidin-4-ylmethylthio)pyridine-3-carboxamide N-(3,5-Dimethylphenyl)-2-[2-[4-(2-hydroxyethyl)piperazin-1-yl)pyrimidin-4-ylmethylthio]pyridine-3-carboxamide N-(3,5-Dimethylphenyl)-2-[2-(4-methylpiperazin-1-yl)pyrimidin-4-ylmethylthio]pyridine-3-carboxamide 2-[2-(piperazin-1-yl)pyrimidin-4-ylmethylthio]-N-(3-trifluorophenyl)pyridine-3-carboxamide The compound of the present invention can be synthesized according to the following methods. Each specific process for synthesizing the present compounds is described in detail in later Examples (section of Production Examples). The term "Hal" used in the following Synthetic Routes represents a halogen atom.

The main Synthetic Routes for synthesizing the compound of the present invention are divided roughly into the two Routes (Synthetic Route A, B) described below, and the suitable methods can be chosen according to the kind of substituents.

Compound (I) of the present invention can be synthesized according to Synthetic Route A. Namely, Compound (III) can be given by reacting Compound (IV) with primary or secondary amine (V) in an organic solvent such as N,N-dimethylformamide (DMF), in the presence of a condensing agent such as O-(7-azabenzotriazol-1-yl)-1,1,3,3-tetramethyluronium hexafluorophosphate (HATU), and a base such as N,N-diisopropylethylamine (DIEA) at room temperature to 50° C. for 1 hour to 24 hours. Then, Compound (I) of the present invention can be given by reacting Compound (III) with Compound (II) in an organic solvent such as DMF, in the presence of a base such as triethylamine (TEA) at room temperature to 50° C. for 1 hour to 24 hours.

[Synthetic Route A]

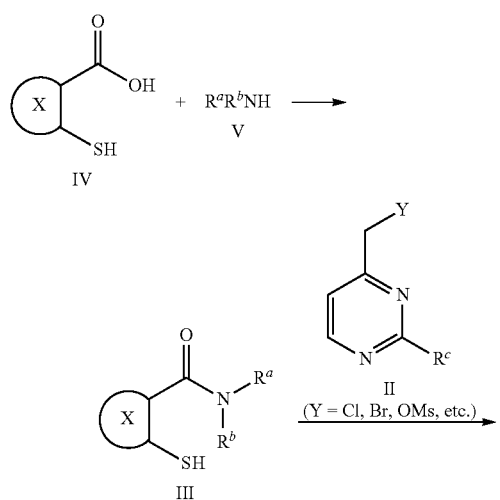

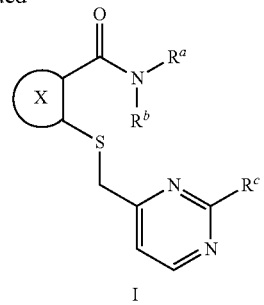

Compound (I) of the present invention can also be synthesized according to Synthetic Route B. Namely, Compound (VI) can be given by reacting Compound (II) with Compound (IV) in an organic solvent such as DMF, in the presence of a base such as TEA, at room temperature to 50° C. for 1 hour to 24 hours. Then, Compound (I) of the present invention can be given by reacting Compound (VI) with primary or secondary amine (V) in an organic solvent such as DMF, in the presence of a condensing agent such as HATU and a base such as DIEA, at room temperature to 50° C., for 1 hour to 24 hours.

[Synthetic Route B]

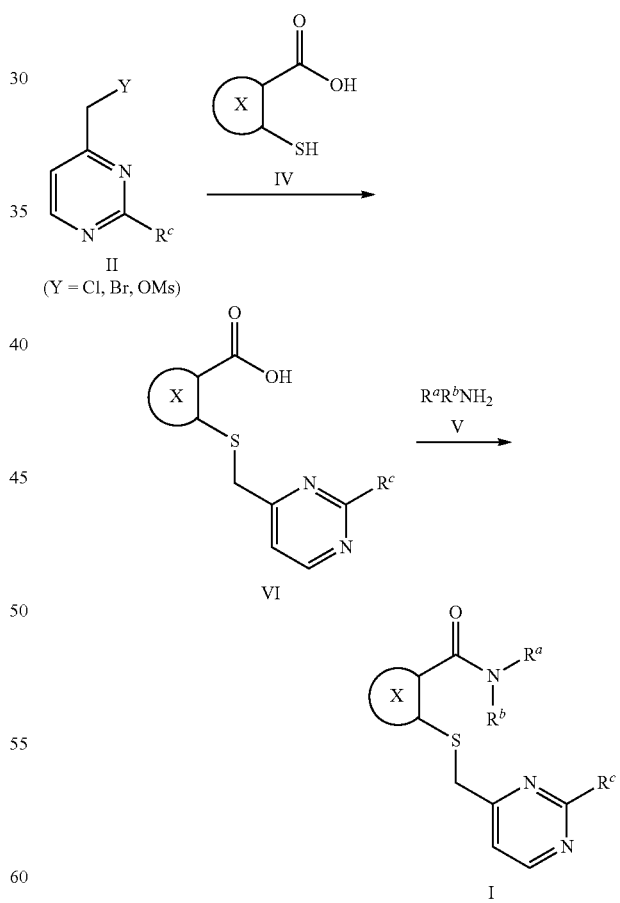

$R^c$ group of Compound (I) of the present invention, given by the Main Synthetic Route, can be converted by the methods below.

When Compound (Ia) of the present invention has amino (—$NHR^d$) group as $R^c$ group, ($R^eCO$) group can be introduced to the amino (—NHR$^d$) group according to Synthetic Route C. Namely, Compound (Ib) of the present invention can be given by reacting Compound (Ia) obtained by the above mentioned methods, with an acylating agent (VIIa, VIIb) such as acetic anhydride or acetyl chloride, in an organic solvent such as DMF, or in the absence of solvent, in the presence of a base such as pyridine, at room temperature to 50° C., for 1 hour to 24 hours.

[Synthetic Route C]

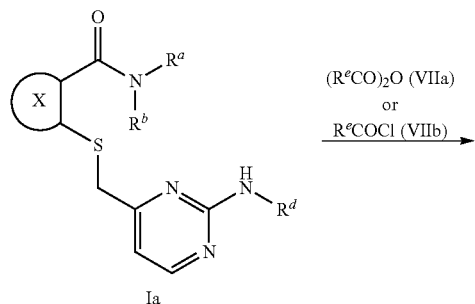

On the other hand, when Compound (Ic) of the present invention has methylsulfinyl (—S(=O)Me) group as R$^c$ group, the methylsulfinyl group can be converted to amino (—NR$^f$R$^g$) group according to Synthetic Route D. Namely, Compound (Id) of the present invention can be given by reacting Compound (Ic) obtained by the above mentioned method, with primary or secondary amine (VIII), in an organic solvent such as DMF or in the absence of solvent, at room temperature to 100° C., for 1 hour to 12 hours.

[Synthetic Route D]

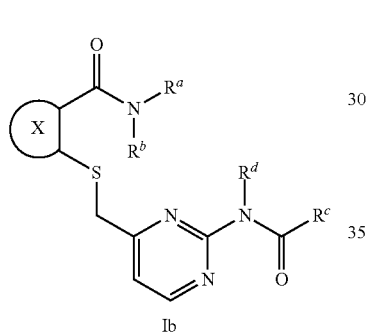

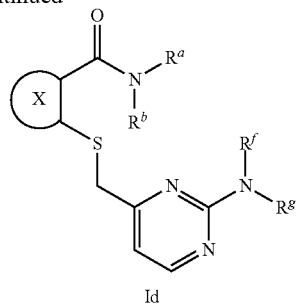

Compound (II) to be used in the Main Synthetic Route can be synthesized according to Synthetic Route E, F, or G.

Compound (IIa) can be synthesized according to Synthetic Route E. Namely, Compound (IIa) can be given by reacting Compound (IX) in an organic solvent such as benzene, in the presence of a radical initiator such as 2,2'-azobisisobutyronitrile and a halogenation agent such as N-bromosuccinimide, under reflux for 1 hour to 12 hours.

[Synthetic Route E]

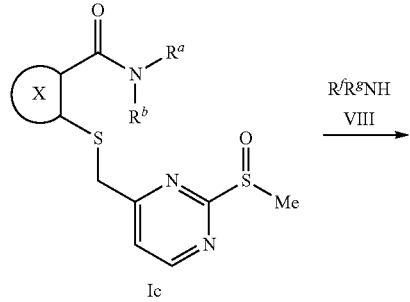

Compounds (IIa, b) can be given by treating Compound (X) in an organic solvent such as methanol, in the presence of a reducing agent such as sodium borohydride to give Alcohol (XI), which is then treated in an organic solvent such as methylene chloride, using a halogenation agent such as thionyl chloride, at 0° C. to 50° C. for 1 hour to 24 hours to give Halogen Compound (IIa); alternatively, methanesulfonyl ether (IIb) can be given by reacting with methanesulfonyl chloride in the presence of a base such as TEA.

[Synthetic Route F]

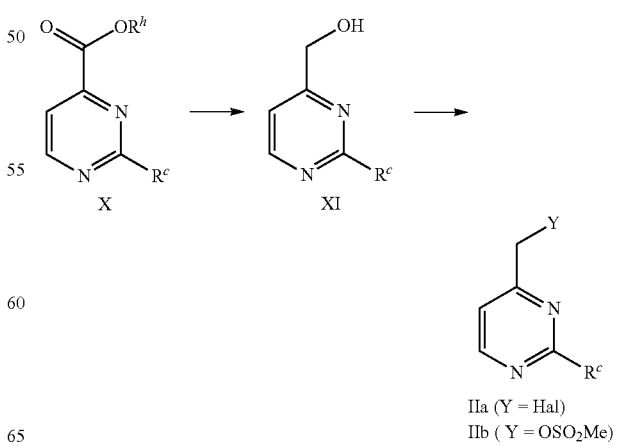

Compound (IId) with methylsulfinyl (—S(=O)Me) group as R$^c$ group can be synthesized according to Synthetic Route G. Namely, Compound (IId, R$^c$:—S(=O)Me) can be given Compound (Xb) with amino group (—NR$^f$R$^g$) as R$^c$ group, can be given by reacting compound (XII) with guanidines (XIV) under similar conditions.

[Synthetic Route H]

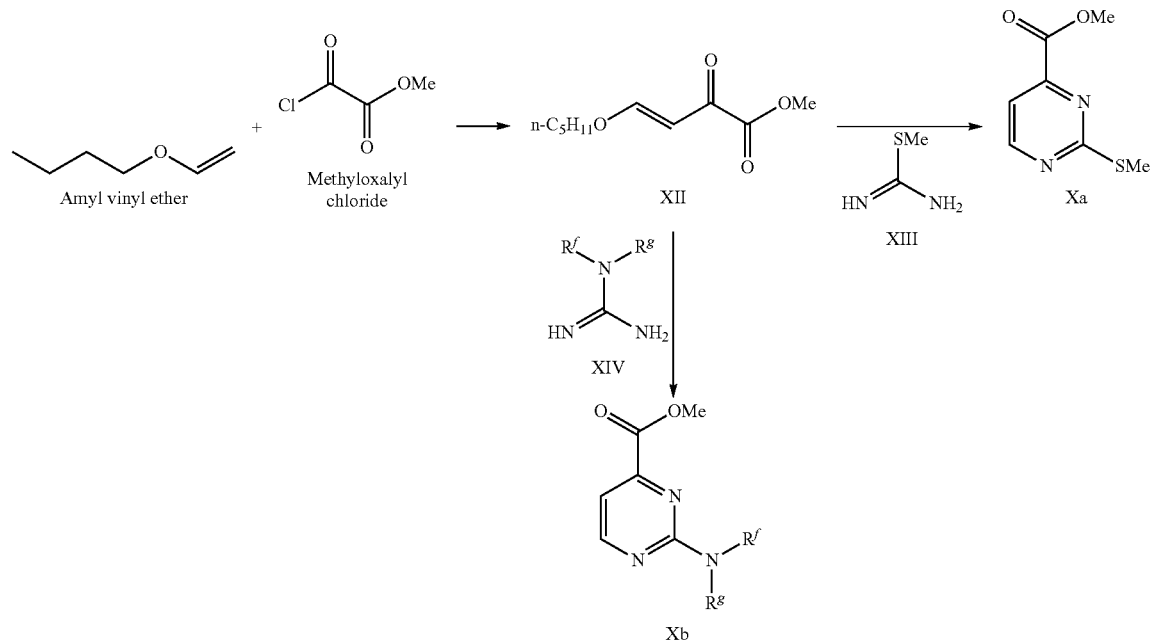

by oxidizing Compound (IIc, R$^c$:—SMe), prepared according to Synthetic Route F, in an organic solvent such as methylene chloride, in the presence of m-chloroperoxybenzoic acid, at 0° C. to 50° C. for 1 hour to 24 hours.

[Synthetic Route G]

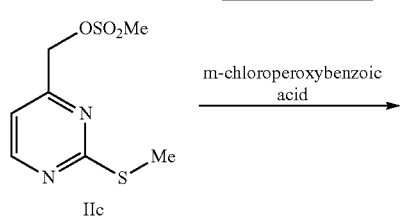

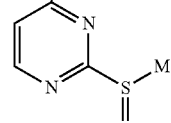

IId

As shown in Synthetic Route H, Compound (X) was synthesized using compounds described in JP-A-2003-89690 "Synthetic method of 2-substituted thiopyridine-4-carboxylic acid ester". Namely, Compound (Xa) having methylthio group (—SMe) as R$^c$ group, can be given by reacting Compound (XII) with methylisothiourea (XIII) in an organic solvent such as propionitrile under reflux. On the other hand, Compound (Xc) can be synthesized according to Synthetic Route I. Namely, Compound (XVI) can be given by reacting Compound (XV) with Compound (VIII) in an organic solvent such as methanol, at room temperature to 80° C. for 15 minutes to 5 hours. Then, Compound (Xc) can be given by reacting the resulting intermediate (XVII) by alkali hydrolysis in the presense of a base such as sodium hydroxide, with alkylating agent such as methyl iodide, in the presence of a base such as sodium hydrogencarbonate at room temperature for 1 hour to 24 hours.

[Synthetic Route I]

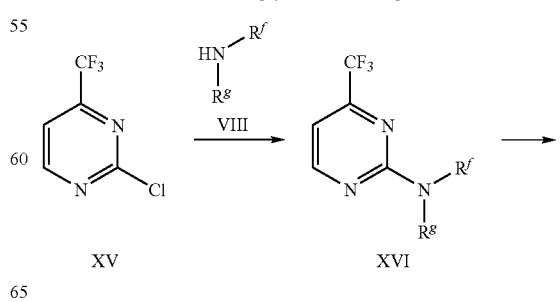

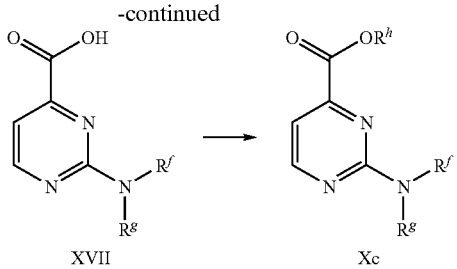

According to Synthetic Route J, Compound (I) of the present invention can be converted to Compound (XVIII) of the present invention with a corresponding sulfoxide. Namely, Compound (I) of the present invention can be synthesized according to Main Synthetic Route A, B and Synthetic Route C, D. Compound (XVIII) of the present invention can be given by oxidizing Compound (I) of the present invention using m-chloroperoxybenzoic acid, in an organic solvent such as methylene chloride at 0° C. to 50° C., for 1 hour to 24 hours.

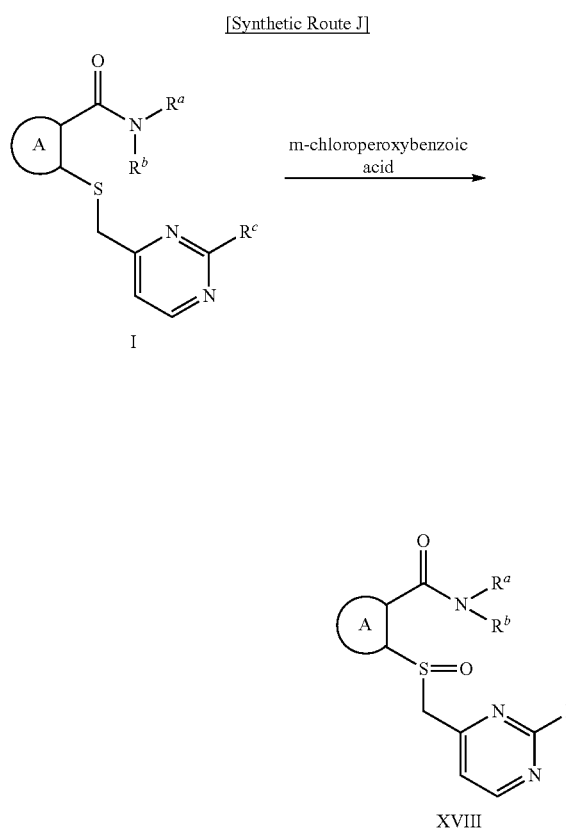

The compound of the present invention prepared by the above synthetic Routes can be converted into the above-mentioned salts, hydrate or solvate using widely-used techniques.

In order to find the usefulness of the compound of the present invention, a test for inhibitory effects of the compound of the present invention on cell proliferation was carried out using a VEGF-induced HUVEC proliferation reaction evaluation system (HUVEC: human umbilical vein endothelial cells), which is a method of evaluating antiangiogenic effects of drugs, and the antiangiogenic effects of the compounds were evaluated. As will be described in detail in the following Examples (in the section of Pharmacological Tests), it was found that the compound of the present invention exhibits an excellent cell proliferation inhibitory action and have an antiangiogenic effect.

As described above, it has been reported that angiogenesis is deeply involved in diseases such as cancer, rheumatoid arthritis, age-related macular degeneration, diabetic retinopathy, retinopathy of prematurity, retinal vein occlusion, polypoid choroidal angiopathy, diabetic macular edema, psoriasis vulgaris and atherosclerosis. Therefore, the compound of the present invention is greatly expected to be used as a therapeutic agent for these diseases associated with angiogenesis.

The compound of the present invention can be administered orally or parenterally. Examples of the dosage form for administration include a tablet, a capsule, a granule, a powder, an injection, an ointment, an eye drop, an ophthalmic ointment and the like. Such a preparation can be prepared by a widely used technique.

For example, an oral preparation such as a tablet, a capsule, a granule or a powder can be prepared by optionally adding an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl p-hydroxybenzoate or benzyl alcohol; a corrigent such as a sweetener, a sour agent or a flavor, or the like.

A parenteral preparation such as an injection or an eye drop can be prepared by optionally adding a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polyoxyethylene sorbitan monoolate, polyoxyl 40 stearate or polyoxyethylene hydrogenated castor oil; a stabilizer such as sodium citrate or sodium edetate; a preservative such as benzalkonium chloride, paraben, benzethonium chloride, p-hydroxybenzoate ester, sodium benzoate or chlorobutanol; a pH adjusting agent such as hydrochloric acid, citric acid, phosphoric acid, glacial acetic acid, sodium hydroxide, sodium carbonate or sodium hydrogencarbonate solution; a soothing agent such as benzyl alcohol, or the like.

The present invention also relates to a method of treating a disease associated with angiogenesis. The dose of the compound of the present invention can be appropriately selected depending on the symptoms, age, dosage form or the like. For example, in the case of an oral preparation, it can be administered in an amount of generally 0.01 to 1,000 mg, preferably 1 to 100 mg per day in a single dose or several divided doses. Further, in the case of an eye drop, a preparation containing the compound of the present invention at a concentration of generally 0.0001 to 10% (w/v), preferably 0.01 to 5% (w/v) can be administered in a single dose or several divided doses.

Hereinafter, Production Examples of the compound of the present invention, Preparation Examples and results of Pharmacological Tests will be described. However, these

PRODUCTION EXAMPLE

Reference Example 1

2-Dimethylamino-4-trifluoromethylpyrimidine (Reference Compound No. 1-1)

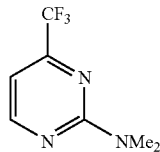

2-Chloro-4-trifluoromethylpyrimidine (600 μL, 5.0 mmol) was dissolved with 2.0M dimethylamine in methanol (10 mL), and stirred for 2 hours in a sealed tube at 60° C. The reaction mixture was diluted with ethyl acetate (50 mL), and the whole was washed with water (50 mL) and dried over anhydrous magnesium sulfate. The solvent was evaporated under reduced pressure to give 640 mg of the title Reference Compound as a colorless oil (Yield: 0.67%).

$^1$H-NMR (400 MHz, CDCl$_3$)

δ 3.22 (s, 6H), 6.72 (d, J=4.9 Hz, 1H), 8.48 (d, J=4.9 Hz, 1H)

Reference Example 2

2-Dimethylamino-4-methoxycarbonylpyrimidine (Reference Compound No. 2-1)

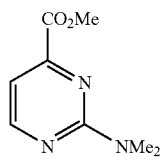

2-Dimethylamino-4-trifluoromethylpyrimidine (320 mg, 1.7 mmol, Reference Compound No. 1-1) and sodium hydroxide (670 mg, 17 mmol) were suspended in a mixed solvent of methanol (5.0 mL) and water (5.0 mL), and then the mixture was stirred while radiated with microwave for 2 and a half hours at 160° C. in a sealed tube. The reaction mixture was diluted with ethyl acetate (30 mL), and extracted with water (30 mL), and then extracted with saturated aqueous sodium hydrogencarbonate solution (30 mL). The extracted aqueous layer was adjusted to pH7 with 6M hydrochloric acid, and was concentrated under reduced pressure. The remaining residue was suspended in N,N-dimethylformamide (5.0 mL), then sodium hydrogencarbonate solution (1.3 g, 14 mmol) and methyl iodide (0.87 mL, 17 mmol) were added thereto, and the whole was stirred for 23 hours at room temperature. The reaction mixture was diluted with ethyl acetate (100 mL), washed twice with saturated aqueous sodium hydrogencarbonate solution (100 mL), and then washed twice with brine (100 mL), and dried over anhydrous magnesium sulfate. The solvent was evaporated under reduced pressure, the residue was purified by silica gel column chromatography to give 28 mg of the title Reference Compound as a colorless needle (Yield: 9.3%)

$^1$H-NMR (500 MHz, CDCl$_3$)

δ 3.24 (s, 6H), 3.95 (d, J=0.6 Hz, 3H), 7.07 (d, J=4.8 Hz, 1H), 8.49 (dd, J=4.8, 0.6 Hz, 1H)

Reference Example 3

2-Amino-4-methoxycarbonylpyrimidine (Reference Compound No. 3-1)

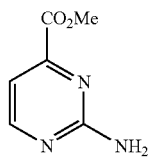

Triethylamine (29 mL, 210 mmol) was added to a suspension of methyl 4-butoxy-2-oxo-3-butenate (37 g, 200 mmol, JP-A-2003-89690) and guanidine hydrochloride (23 g, 240 mmol) in propionitrile (50 mL), and the mixture was stirred for 4 hours at 100° C. The reaction mixture was concentrated under reduced pressure, and the residue was purified by silica gel column chromatography to give 18 g as the mixture of the title Reference Compound and the butyl ester form of the title Reference compound as a gray-white solid (Yield: 60%).

$^1$H-NMR (500 MHz, DMSO-d$_6$)

δ 3.85 (s, 3H), 6.99-7.06 (m, 3H), 8.48 (d, J=4.8 Hz, 1H)

As described below, Reference Compounds Nos. 3-2 to 3-4 were obtained following the method similar to that of Reference Compound No. 3-1, using the corresponding compounds selected from compounds which are on the market or compounds which are commonly known.

4-Methoxycarbonyl-2-methylthiopyrimidine (Reference Compound No. 3-2)

$^1$H-NMR (500 MHz, CDCl$_3$)

δ 2.62 (s, 3H), 4.00 (s, 3H), 7.61 (d, J=4.9 Hz, 1H), 8.74 (d, J=4.9 Hz, 1H)

2-Methylamino-4-methoxycarbonylpyrimidine (Reference Compound No. 3-3)

$^1$H-NMR (400 MHz, DMSO-d$_6$)

δ 2.82 (d, J=4.9 Hz, 3H), 3.85 (s, 3H), 7.04 (d, J=4.9 Hz, 1H), 7.58 (br s, 1H), 8.52 (br s, 1H)

2-Acetylamino-4-methoxycarbonylpyrimidine (Reference Compound No. 3-4)

$^1$H-NMR (400 MHz, DMSO-d$_6$)

δ 2.19 (s, 3H), 3.91 (s, 3H), 7.65 (d, J=4.9 Hz, 1H), 8.91 (d, J=4.9 Hz, 1H), 10.90 (s, 1H)

Reference Example 4

2-Amino-4-hydroxymethylpyrimidine (Reference Compound No. 4-1)

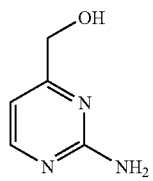

2-Amino-4-methoxycarbonylpyrimidine (3.0 g, 20 mmol, Reference Compound No. 3-1) was suspended in a mixture solvent of ethanol (150 mL) and dichloromethane (20 mL), then sodium borohydride (2.2 g, 59 mmol) was added thereto at room temperature, and the whole was stirred for 24 hours. Acetone (20 mL) was added gradually under ice-cooling, and then 2M hydrochloric acid was added until the bubbles were no longer formed. Saturated aqueous sodium hydrogencarbonate solution was added to adjust the pH of the reaction mixture to 8, and the precipitated solid was filtered out. The filtrate was concentrated under reduced pressure, then suspended in a 10% methanol-chloroform solution, and the mixture was filtered again with silica gel (5.0 g). The filtrate was evaporated under reduced pressure, the precipitated solid was filtered off with ethyl acetate, and dried under reduced pressure to give 1.8 g of the title Reference Compound as a pale yellow solid (Yield: 73%)

$^1$H-NMR (400 MHz, DMSO-$d_6$)

δ 4.30 (s, 2H), 5.35 (s, 1H), 6.48 (s, 2H), 6.65 (d, J=4.9 Hz, 1H), 8.19 (d, J=4.9 Hz, 1H)

As described below, Reference Compounds Nos. 4-2 to 4-4 were obtained following the method similar to that of Reference Compound No. 4-1, using the corresponding compounds selected from Reference Compounds Nos. 3-1 to 3-4, and compounds which are on the market or compounds which are commonly known.

2-Dimethylamino-4-hydroxymethylpyrimidine (Reference Compound No. 4-2)

$^1$H-NMR (400 MHz, CDCl$_3$)

δ 3.21 (s, 6H), 3.88 (s, 1H), 4.57 (s, 2H), 6.35 (d, J=4.9 Hz, 1H), 8.24 (d, J=4.9 Hz, 1H)

2-Acetylamino-4-hydroxymethylpyrimidine (Reference Compound No. 4-3)

$^1$H-NMR (400 MHz, DMSO-$d_6$)

δ 2.17 (s, 3H), 4.48 (d, J=5.4 Hz, 2H), 5.60 (t, J=5.4 Hz, 1H), 7.22 (d, J=4.9 Hz, 1H), 8.61 (d, J=4.9 Hz, 1H), 10.46 (s, 1H)

4-Hydroxymethyl-2-methylthiopyrimidine (Reference Compound No. 4-4)

$^1$H-NMR (400 MHz, CDCl$_3$)

δ 2.58 (s, 3H), 3.27 (t, J=4.9 Hz, 1H), 4.70 (d, J=4.9 Hz, 2H), 6.96 (d, J=5.0 Hz, 1H), 8.47 (d, J=5.0 Hz, 1H)

Reference Example 5

2-Amino-4-(tert-butyldimethylsilyloxymethyl)pyrimidine (Reference Compound No. 5-1)

2-Amino-4-hydroxymethylpyrimidine (750 mg, 6.0 mmol, Reference Compound No. 4-1) and tert-butyldimethylsilyl chloride (990 mg, 6.6 mmol) were suspended in anhydrous N,N-dimethylformamide (8.0 mL), then imidazole (0.90 g, 13 mmol) was added thereto and the mixture was stirred for 1 hour at room temperature. The reaction mixture was diluted with ethyl acetate (50 mL), washed twice with saturated aqueous sodium hydrogencarbonate solution (50 mL), and then washed with brine (50 mL), and dried over anhydrous magnesium sulfate. Then the solvent was evaporated under reduced pressure, the precipitated solid was filtered off with 50% ethyl acetate-n-hexane solution, and dried under reduced pressure to give 1.2 g of the title Reference Compound as a white solid (Yield: 84%).

$^1$H-NMR (400 MHz, CDCl$_3$)

δ 0.11 (s, 6H), 0.95 (s, 9H), 4.59 (s, 2H), 5.03 (s, 2H), 6.87 (d, J=5.1 Hz, 1H), 8.29 (d, J=5.1 Hz, 1H)

Reference Example 6

4-tert-Butyldimethylsilyloxymethyl-2-(methylamino)pyrimidine (Reference Compound No. 6-1)

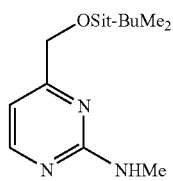

Under a nitrogen atmosphere, a solution of 2-amino-4-(tert-butyldimethylsilyloxymethyl)pyrimidine (200 mg, 0.84 mmol, Reference Compound No. 5-1) in anhydrous tetrahydrofuran (4.0 mL) was added dropwise to a suspension of sodium hydride (60%, 37 mg, 0.92 mmol) in anhydrous tetrahydrofuran (1.0 mL) under ice-cooling. The mixture was stirred for 15 minutes under ice-cooling, then methyl iodide (57 μL, 0.92 mmol) was added thereto, and the mixture was stirred for 2 hours at room temperature. The reaction mixture was poured into brine (30 mL), then extracted with ethyl acetate (30 mL). The extract was dried over anhydrous magnesium sulfate, and the solvent was evaporated under reduced pressure. The residue was purified by silica gel column chromatography to give 43 mg of the title Reference Compound as a colorless oil (Yield: 20%).

$^1$H-NMR (500 MHz, CDCl$_3$)

δ 0.11 (s, 6H), 0.95 (s, 9H), 2.99 (d, J=4.9 Hz, 3H), 4.59 (s, 2H), 5.06 (s, 1H), 6.77 (d, J=4.9 Hz, 1H), 8.29 (d, J=4.9 Hz, 1H)

Reference Example 7

4-Hydroxymethyl-2-methylaminopyrimidine (Reference Compound No. 7-1)

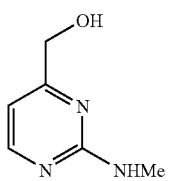

4-tert-Butyldimethylsilyloxymethyl-2-methylaminopyrimidine (40 mg, 0.16 mmol, Reference Compound No. 6-1) was dissolved in tetrahydrofuran (3.0 mL), then a solution of tetrabutylammonium fluoride trihydrate (55 mg, 0.17 mmol) in tetrahydrofuran (3.0 mL) was added thereto, and the mixture was stirred for 40 minutes at room temperature. The reaction mixture was concentrated under reduced pressure. The residue was suspended into 25% methanol-chloroform solution, and the mixture was filtered with silica gel (2.0 g). The filtrate was concentrated under reduced pressure to give 60 mg of the mixture of the title Reference Compound and tetrabutylammonium fluoride as a brown oil.

$^1$H-NMR (500 MHz, CDCl$_3$)

δ 3.01 (s, 3H), 3.30 (m, 1H), 4.56 (s, 2H), 6.50 (d, J=5.2 Hz, 1H), 8.22 (d, J=5.2 Hz, 1H)

Reference Example 8

2-Amino-4-methanesulfonyloxymethylpyrimidine (Reference Compound No. 8-1)

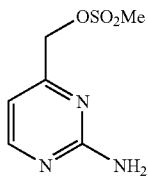

N,N-Diisopropylethylamine (490 μL, 2.9 mmol) and methanesulfonyl chloride (110 μL, 1.5 mmol) were added to a suspension of 2-amino-4-hydroxymethylpyrimidine (170 mg, 1.3 mmol, Reference Compound No. 4-1) in anhydrous tetrahydrofuran (5.0 mL) under ice-cooling, and the mixture was stirred for 7 hours at room temperature. The reaction mixture was diluted with ethyl acetate (300 mL), washed with water (300 mL), and then dried over anhydrous magnesium sulfate. The solvent was evaporated under reduced pressure, the precipitated solid was filtered off with ethyl acetate, and dried under reduced pressure to give 140 mg of the title Reference Compound as a white solid (Yield: 53%).

$^1$H-NMR (500 MHz, DMSO-d$_6$)

δ 3.30 (s, 3H), 5.06 (s, 2H), 6.63 (d, J=5.2 Hz, 1H), 6.78 (s, 2H), 8.28 (d, J=5.2 Hz, 1H)

As described below, Reference Compound No. 8-2 was obtained following the method similar to that of Reference Compound No. 8-1, using the corresponding compounds selected from Reference Compound No. 4-4, and compounds which are on the market or compounds which are commonly known.

4-Methanesulfonyloxymethyl-2-methylthiopyrimidine (Reference Compound No. 8-2)

$^1$H-NMR (500 MHz, CDCl$_3$)

δ 2.57 (s, 3H), 3.14 (s, 3H), 5.22 (s, 2H), 7.13 (d, J=4.9 Hz, 1H), 8.58 (d, J=4.9 Hz, 1H)

Reference Example 9

4-Methanesulfonyloxymethyl-2-methylsulfinylpyrimidine (Reference Compound No. 9-1)

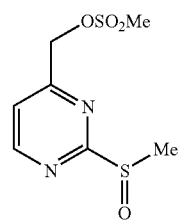

m-Chloroperoxybenzoic acid (75%, 2.4 g, 10 mmol) was added to a solution of 4-methanesulfonyloxymethyl-2-methylthiopyrimidine (2.4 g, 10 mmol, Reference Compound No. 8-2) in anhydrous methylene chloride (30 mL) and the mixture was stirred for 15 minutes under ice-cooling. m-Chloroperoxybenzoic acid (0.29 g, 1.3 mmol) was added thereto and the whole was stirred for 10 minutes under ice-cooling. The reaction mixture was diluted with ethyl acetate (100 mL), washed twice with saturated aqueous sodium hydrogencarbonate solution (30 mL), and then washed with brine (30 mL). The aqueous layer was extracted twice with chloroform (100 mL), then the extract was mixed with the ethyl acetate layer, and the whole was dried over anhydrous magnesium sulfate. The solvent was concentrated under reduced pressure to give 2.2 g of the title Reference Compound as a colorless oil (Yield: 88%).

$^1$H-NMR (500 MHz, DMSO-d$_6$)

δ 2.97 (s, 3H), 3.21 (s, 3H), 5.42 (s, 2H), 7.62 (d, J=4.9 Hz, 1H), 8.93 (d, J=4.9 Hz, 1H)

Reference Example 10

4-Bromomethylpyrimidine (Reference Compound No. 10-1)

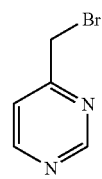

2,2'-Azobisisobutylonitrile (170 mg, 1.0 mmol) was added to a solution of 4-methylpyrimidine (0.97 mL, 11 mmol) and N-bromosuccinimide (1.9 g, 11 mmol) in anhydrous benzene (25 mL), and the mixture was stirred for 16 hours at 70° C. The insoluble matter was filtered out, and the solvent was evaporated under reduced pressure. The resulting residue was purified by silica gel column chromatography to give 400 mg of the title Reference Compound as a yellow oil (Yield: 21%).

$^1$H-NMR (500 MHz, DMSO-$d_6$)

δ 4.65 (s, 2H), 7.67 (dd, J=4.9, 1.5 Hz, 1H), 8.83 (d, J=4.9 Hz, 1H), 9.18 (d, J=1.5 Hz, 1H)

Reference Example 11

2-Acetylamino-4-chloromethylpyrimidine (Reference Compound No. 11-1)

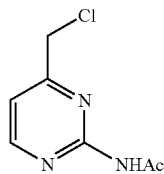

Thionyl chloride (0.18 mL, 2.4 mmol) was added to a suspension of 2-acetylamino-4-hydroxymethylpyrimidine (290 mg, 1.7 mmol, Reference Compound No. 4-3) in anhydrous methylene chloride (10 mL) at room temperature, and the mixture was stirred for 30 minutes. The solvent was evaporated under reduced pressure, then water (50 mL) and ethyl acetate (100 mL) were added thereto and the mixture was separated into the organic layer and the aqueous layer, and the aqueous layer was extracted twice with ethyl acetate (50 mL). The whole organic layer was dried over anhydrous magnesium sulfate, and the solvent was evaporated under reduced pressure to give 68 mg of the title Reference Compound as a yellow solid (Yield: 18%).

$^1$H-NMR (400 MHz, DMSO-$d_6$)

δ 2-0.19 (s, 3H), 4.71 (s, 2H), 7.29 (d, J=5.1 Hz, 1H), 8.69 (d, J=5.1 Hz, 1H), 10.64 (s, 1H)

Reference Example 12

2-(2-Aminopyrimidin-4-ylmethylthio)nicotinic Acid (Reference Compound No. 12-1)

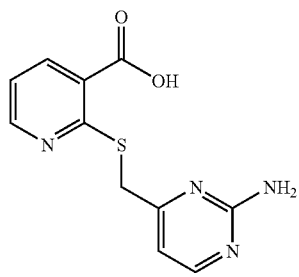

2-Amino-4-methanesulfonyloxymethylpyrimidine (580 mg, 2.9 mmol, Reference Compound No. 8-1) was suspended in N,N-dimethylformamide (15 mL), and 2-mercaptonicotinic acid (400 mg, 2.6 mmol) and triethylamine (1.2 mL, 8.6 mmol) were added thereto under ice-cooling, and the mixture was stirred for 21 hours at room temperature. The reaction mixture was diluted with ethyl acetate (50 mL), and extracted with water (50 mL) and saturated aqueous sodium hydrogencarbonate solution (30 mL). 2M hydrochloric acid was added to the aqueous layer until bubbles were no longer formed, and the precipitated solid was filtered off. The solid was dried at 55° C. under reduced pressure, to give 470 mg of the title Reference Compound as a white solid (Yield: 70%).

$^1$H-NMR (400 MHz, DMSO-$d_6$)

δ 4.23 (s, 2H), 6.60 (s, 2H), 6.61 (d, J=5.1 Hz, 1H), 7.25 (dd, J=7.6, 4.9 Hz, 1H), 8.10 (d, J=5.1 Hz 0.1H), 8.22 (dd, J=7.6, 1.8 Hz, 1H), 8.60 (dd, J=4.9, 1.8 Hz, 1H), 13.48 (s, 1H)

As described below, Reference Compounds Nos. 12-2 to 12-6 were obtained following the method similar to that of Reference Compound No. 12-1, using the corresponding compounds selected from Reference Compounds Nos. 8-1, 8-2, 9-1, 10-1, 11-1, and compounds which are on the market or compounds which are commonly known.

2-(2-Aminopyrimidin-4-ylmethylthio)benzoic Acid (Reference Compound No. 12-2)

$^1$H-NMR (500 MHz, DMSO-$d_6$)

δ 4.05 (s, 2H), 6.67-6.69 (m, 3H), 7.21 (td, J=7.3, 1.4 Hz, 1H), 7.45-7.49 (m, 2H), 7.88 (dd, J=7.3, 1.4 Hz, 1H), 8.16 (d, J=5.0 Hz, 1H), 13.08 (s, 1H)

3-(2-Aminopyrimidin-4-ylmethylthio)thiophene-2-carboxlic Acid (Reference Compound No. 12-3)

$^1$H-NMR (500 MHz, DMSO-$d_6$)

δ 4.19 (s, 2H), 6.74 (d, J=5.5 Hz, 1H), 7.01 (s, 2H), 7.22 (d, J=5.5 Hz, 1H), 7.85 (d, J=5.5 Hz, 1H), 8.20 (d, J=5.5 Hz, 1H), 13.00 (s, 1H)

2-(Pyrimidin-4-ylmethylthio)nicotinic Acid (Reference Compound No. 12-4)

$^1$H-NMR (500 MHz, DMSO-$d_6$)

δ 4.47 (s, 2H), 7.26 (dd, J=7.6, 4.6 Hz, 1H), 7.59 (dd, J=5.4, 1.5 Hz, 1H), 8.24 (dd, J=7.6, 1.5 Hz, 1H), 8.59 (dd, J=4.6, 1.5 Hz, 1H), 8.68 (d, J=5.4 Hz, 1H), 9.08 (d, J=1.5 Hz, 1H), 13.52 (s, 1H)

2-(2-Methylthiopyrimidin-4-ylmethylthio)nicotinic Acid (Reference Compound No. 12-5)

$^1$H-NMR (500 MHz, CDCl$_3$)

δ 2.55 (s, 3H), 4.48 (s, 2H), 7.10-7.13 (m, 2H), 8.30 (dd, J=7.6, 1.9 Hz, 1H), 8.38 (d, J=5.4 Hz, 1H), 8.56 (dd, J=4.6, 1.9 Hz, 1H)

2-(2-Methylsulfinylpyrimidin-4-ylmethylthio)nicotinic Acid (Reference Compound No. 12-6)

$^1$H-NMR (500 MHz, DMSO-$d_6$)

δ 2.73 (s, 3H), 4.55 (s, 2H), 7.27 (dd, J=7.6, 4.9 Hz, 1H), 7.71 (d, J=5.2 Hz, 1H), 8.25 (dd, J=7.6, 1.5 Hz, 1H), 8.58 (dd, J=4.9, 1.5 Hz, 1H), 8.85 (d, J=5.2 Hz, 1H), 13.59 (br s, 1H)

Reference Example 13

N-(3,5-Dimethylphenyl)-2-thioxo-1,2-dihydropyridine-3-carboxamide (Reference Compound No. 13-1)

2-Mercaptonicotinic acid (90 g, 0.58 mol) was suspended in N,N-dimethylformamide (660 mL) under ice-cooling, then carbonyldiimidazole (110 g, 0.70 mol) was added thereto, and the whole was stirred for 2 hours at room temperature. Water (5.4 mL) was added thereto, and the whole was stirred for 40 minutes, and then 3,5-xylidine (76 mL, 0.61 mol) was added thereto and the resulting mixture was stirred at 60° C. for 16 hours. The mixture was allowed to stand, and then water (1.3 L) was added, and the precipitated solid was filtered off. The solid was dried at 45° C. under reduced pressure to give 130 g of the title Reference Compound as a yellow solid (Yield: 89%).

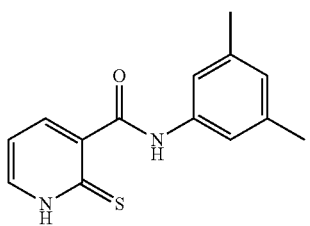

¹H-NMR (500 MHz, DMSO-$d_6$)

δ 2.27 (s, 6H), 6.77 (s, 1H), 7.10 (dd, J=7.6, 6.0 Hz, 1H), 7.34 (s, 2H), 8.03 (dd, J=6.0, 1.8 Hz, 1H), 8.55 (dd, J=7.6, 1.8 Hz, 1H), 12.90 (s, 1H), 14.18 (s, 1H)

As described below, Reference Compounds Nos. 13-2 to 13-4 were obtained following the method similar to that of Reference Compound No. 13-1, using the corresponding compounds selected from compounds which are on the market or compounds which are commonly known.

2-Thioxo-N-(4-trifluoromethoxyphenyl)-1,2-dihydropyridine-3-carboxamide (Reference Compound No. 13-2)

¹H-NMR (500 MHz, DMSO-$d_6$)

δ 7.08 (dd, J=7.5, 5.8 Hz, 1H), 7.39 (d, J=8.8 Hz, 2H), 7.82 (d, J=8.8 Hz, 2H), 8.03 (dd, J=5.8, 1.8 Hz, 1H), 8.48 (dd, J=7.5, 1.8 Hz, 1H), 12.91 (s, 1H), 14.19 (s, 1H)

N-(4-Chlorophenyl)-2-thioxo-1,2-dihydropyridine-3-carboxamide (Reference Compound No. 13-3)

¹H-NMR (400 MHz, DMSO-$d_6$)

δ 7.08 (dd, J=7.6, 6.1 Hz, 1H), 7.43 (d, J=8.7 Hz, 2H), 7.74 (d, J=8.7 Hz, 2H), 8.03 (dd, J=6.1, 1.8 Hz, 1H), 8.48 (dd, J=7.6, 1.8 Hz, 1H), 12.90 (s, 1H), 14.19 (s, 1H)

N-(Indan-5-yl)-2-thioxo-1,2-dihydropyridine-3-carboxamide (Reference Compound No. 13-4)

¹H-NMR (400 MHz, DMSO-$d_6$)

δ 1.98-2.06 (m, 2H), 2.81-2.89 (m, 4H), 7.09 (dd, J=7.6, 4.8 Hz, 1H), 7.20 (d, J=8.1 Hz, 1H), 7.43 (dd, J=8.1, 2.0 Hz, 1H), 7.62 (s, 1H), 8.03 (dd, J=4.8, 1.7 Hz, 1H), 8.55 (dd, J=7.6, 1.7 Hz, 1H), 12.93 (s, 1H), 14.18 (s, 1H)

Example 1

2-(2-Aminopyrimidin-4-ylmethylthio)-N-(3,5-dimethylphenyl)pyridine-3-carboxamide (Compound No. 1-1)

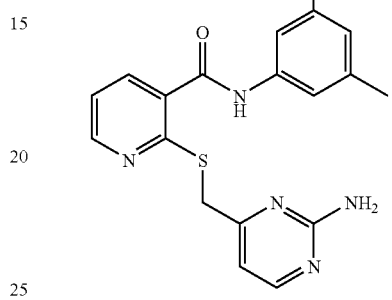

O-(7-Azabenzotriazole-1-yl)-N,N,N',N'-tetrauroniumhexafluorophosphate (110 mg, 0.29 mmol) was added to a solution of 2-(2-aminopyrimidin-4-ylmethylthio)nicotinic acid (60 mg, 0.24 mmol, Reference Compound No. 12-1), 3,5-dimethylaniline (33 μL, 0.27 mmol) and N,N-diisopropylethylamine (0.93 μL, 0.53 mmol) in anhydrous N,N-dimethylformamide (1.0 mL) at room temperature, and the mixture was stirred for 18 hours. Ethyl acetate (30 mL) was added thereto, and then the whole was washed with saturated aqueous sodium hydrogencarbonate solution (50 mL) and brine (50 mL), then the organic layer was dried over anhydrous magnesium sulfate. The solvent was evaporated under reduced pressure, the precipitated solid was filtered off, and washed with 50% diethylether-ethyl acetate solution. The solid was then dried at 60° C. under reduced pressure to give 35 mg of the target compound as a light brown solid (Yield: 41%).

¹H-NMR (500 MHz, DMSO-$d_6$)

δ 2.26 (s, 6H), 4.26 (s, 2H), 6.59 (s, 2H), 6.62 (d, J=4.9 Hz, 1H), 6.76 (s, 1H), 7.27 (dd, J=7.6, 4.9 Hz, 1H), 7.33 (s, 2H), 7.92 (dd, J=7.6, 1.5 Hz, 1H), 8.11 (d, J=4.9 Hz, 1H), 8.55 (dd, J=4.9, 1.5 Hz, 1H), 10.32 (s, 1H)

As described below, Compounds Nos. 1-2 to 1-34 were obtained following the method similar to that of Compound No. 1-1, using the corresponding compounds selected from Reference Compounds Nos. 12-1 to 12-6, compounds which are on the market or compounds which are commonly known.

2-(2-Aminopyrimidin-4-ylmethylthio)-N-(4-chlorophenyl)pyridine-3-carboxamide (Compound No. 1-2)

¹H-NMR (400 MHz, DMSO-$d_6$)

δ 4.27 (s, 2H), 6.60 (s, 2H), 6.62 (d, J=5.1 Hz, 1H), 7.29 (dd, J=7.6, 4.8 Hz, 1H), 7.42 (d, J=9.0 Hz, 2H), 7.74 (d, J=9.0 Hz, 2H), 7.97 (dd, J=7.6, 1.7 Hz, 1H), 8.11 (d, J=5.1 Hz, 1H), 8.57 (dd, J=4.9, 1.7 Hz, 1H), 10.62 (s, 1H)

2-(2-Aminopyrimidin-4-ylmethylthio)-N-(4-trifluoromethoxyphenyl)pyridine-3-carboxamide (Compound No. 1-3)

¹H-NMR (400 MHz, DMSO-d$_6$)
δ 4.27 (s, 2H), 6.60 (s, 2H), 6.62 (d, J=5.2 Hz, 1H), 7.30 (dd, J=7.8, 4.9 Hz, 1H), 7.38 (d, J=8.3 Hz, 2H), 7.82 (d, J=8.3 Hz, 2H), 7.98 (dd, J=7.8, 1.7 Hz, 1H), 8.11 (d, J=5.2 Hz, 1H), 8.57 (dd, J=4.9, 1.7 Hz, 1H), 10.68 (s, 1H)

2-(2-Aminopyrimidin-4-ylmethylthio)-N-(indan-5-yl)pyridine-3-carboxamide (Compound No. 1-4)

¹H-NMR (500 MHz, DMSO-d$_6$)
δ 1.99-2.05 (m, 2H), 2.81-2.89 (m, 4H), 4.26 (s, 2H), 6.59 (s, 2H), 6.62 (d, J=5.1 Hz, 1H), 7.18 (d, J=8.0 Hz, 1H), 7.27 (dd, J=7.6, 4.9 Hz, 1H), 7.39 (d, J=8.0 Hz, 1H), 7.62 (s, 1H), 7.92 (dd, J=7.6, 1.5 Hz, 1H), 8.11 (d, J=5.1 Hz, 1H), 8.56 (dd, J=4.9, 1.5 Hz, 1H), 10.36 (s, 1H)

2-(2-Aminopyrimidin-4-ylmethylthio)-N-(3-methylphenyl)pyridine-3-carboxamide (Compound No. 1-5)

¹H-NMR (400 MHz, CDCl$_3$)
δ 2.31 (s, 3H), 4.27 (s, 2H), 6.59 (s, 2H), 6.62 (d, J=5.0 Hz, 1H), 6.94 (d, J=7.7 Hz, 1H), 7.23 (t, J=7.7 Hz, 1H), 7.28 (dd, J=7.6, 4.9 Hz, 1H), 7.47 (d, J=7.7 Hz, 1H), 7.56 (s, 1H), 7.93 (dd, J=7.6, 1.7 Hz, 1H), 8.11 (d, J=5.0 Hz, 1H), 8.56 (dd, J=4.9, 1.7 Hz, 1H), 10.40 (s, 1H)

2-(2-Aminopyrimidin-4-ylmethylthio)-N-(4-tert-butylphenyl)pyridine-3-carboxamide (Compound No. 1-6)

¹H-NMR (500 MHz, DMSO-d$_6$)
δ 1.28 (s, 9H), 4.26 (s, 2H), 6.59 (s, 2H), 6.62 (d, J=4.9 Hz, 1H), 7.28 (dd, J=7.4, 4.9 Hz, 1H), 7.37 (dd, J=8.9, 2.0 Hz, 2H), 7.61 (d, J=8.9 Hz, 2H), 7.93 (dd, J=7.4, 1.9 Hz, 1H), 8.11 (d, J=4.9 Hz, 1H), 8.56 (dd, J=4.9, 1.9 Hz, 1H), 10.41 (s, 1H)

2-(2-Aminopyrimidin-4-ylmethylthio)-N-(3-isopropylphenyl)pyridine-3-carboxamide (Compound No. 1-7)

¹H-NMR (500 MHz, DMSO-d$_6$)
δ 1.20 (d, J=9.1 Hz, 6H), 2.88 (m, 1H), 4.27 (s, 2H), 6.59 (s, 2H), 6.62 (d, J=4.9 Hz, 1H), 7.00 (d, J=7.6 Hz, 1H), 7.25-7.29 (m, 2H), 7.52 (d, J=8.6 Hz, 1H), 7.60 (s, 1H), 7.95 (dd, J=7.6, 1.9 Hz, 1H), 8.11 (d, J=4.9 Hz, 1H), 8.56 (dd, J=4.7, 1.9 Hz, 1H), 10.42 (s, 1H)

2-(2-Aminopyrimidin-4-ylmethylthio)-N-(5-chloro-2,4-dimethoxyphenyl)pyridine-3-carboxamide (Compound No. 1-8)

¹H-NMR (400 MHz, DMSO-d$_6$)
δ 3.86 (s, 3H), 3.90 (s, 3H), 4.25 (s, 2H), 6.60 (s, 2H), 6.62 (d, J=5.1 Hz, 1H), 6.88 (s, 1H), 7.26 (dd, J=7.6, 4.9 Hz, 1H), 7.71 (s, 1H), 7.95 (d, J=7.6 Hz, 1H), 8.11 (d, J=5.1 Hz, 1H), 8.55 (d, J=4.9 Hz, 1H), 9.74 (s, 1H)

2-(2-Aminopyrimidin-4-ylmethylthio)-N-(4-methoxyphenyl)pyridine-3-carboxamide (Compound No. 1-9)

¹H-NMR (400 MHz, DMSO-d$_6$)
δ 3.74 (s, 3H), 4.26 (s, 2H), 6.60 (s, 2H), 6.62 (d, J=5.1 Hz, 1H), 6.93 (d, J=9.0 Hz, 2H), 7.27 (dd, J=7.6, 4.9 Hz, 1H), 7.61 (d, J=9.0 Hz, 2H), 7.93 (dd, J=7.6, 1.7 Hz, 1H), 8.11 (d, J=5.1 Hz, 1H), 8.55 (dd, J=4.9, 1.7 Hz, 1H), 10.34 (s, 1H)

2-(2-Aminopyrimidin-4-ylmethylthio)-N-(4'-methoxyphenethyl)pyridine-3-carboxamide (Compound No. 1-10)

¹H-NMR (400 MHz, DMSO-d$_6$)
δ 2.75 (t, J=7.3 Hz, 2H), 3.36-3.42 (m, 2H), 3.71 (s, 3H), 4.21 (s, 2H), 6.59 (d, J=5.1 Hz, 1H), 6.60 (s, 2H), 6.85 (dd, J=8.1, 1.9 Hz, 2H), 7.16 (d, J=8.1 Hz, 2H), 7.20 (dd, J=7.6, 4.9 Hz, 1H), 7.72 (dd, J=7.6, 1.7 Hz, 1H), 8.10 (d, J=5.1 Hz, 1H), 8.50 (dd, J=4.9, 1.7 Hz, 1H), 8.59 (t, J=5.6 Hz, 1H)

2-(2-Aminopyrimidin-4-ylmethylthio)-N-(quinolin-6-yl)pyridine-3-carboxamide (Compound No. 1-11)

¹H-NMR (400 MHz, DMSO-d$_6$)
δ 4.28 (s, 2H), 6.59 (s, 2H), 6.63 (d, J=5.7 Hz, 1H), 7.32 (dd, J=7.6, 4.9 Hz, 1H), 7.51 (dd, J=8.3, 4.1 Hz, 1H), 7.90 (m, 1H), 8.00-8.06 (m, 2H), 8.11 (d, J=5.1 Hz, 1H), 8.36 (d, J=7.8 Hz, 1H), 8.53 (s, 1H), 8.60 (dd, J=4.9, 1.7 Hz, 1H), 8.82 (dd, J=4.1, 1.4 Hz, 1H), 10.83 (s, 1H)

2-(2-Aminopyrimidin-4-ylmethylthio)-N-(isoquinolin-3-yl)pyridine-3-carboxamide (Compound No. 1-12)

¹H-NMR (400 MHz, DMSO-d$_6$)
δ 4.28 (s, 2H), 6.60 (s, 2H), 6.63 (d, J=4.9 Hz, 1H), 7.27 (dd, J=7.6, 4.9 Hz, 1H), 7.58 (m, 1H), 7.75 (m, 1H), 7.99 (d, J=8.1 Hz, 1H), 8.04 (dd, J=7.6, 1.7 Hz, 1H), 8.08-8.13 (m, 2H), 8.57 (dd, J=4.9, 1.7 Hz, 1H), 8.60 (s, 1H), 9.20 (s, 1H), 11.18 (s, 1H)

[2-(2-Aminopyrimidin-4-ylmethylthio)pyridin-3-yl]morpholinomethanone (Compound No. 1-13)

¹H-NMR (500 MHz, DMSO-d$_6$)
δ 3.11 (br s, 2H), 3.50 (br s, 2H), 3.63 (d, J=5.5 Hz, 4H), 4.31 (s, 2H), 6.56 (d, J=4.9 Hz, 1H), 6.61 (s, 2H), 7.24 (dd, J=7.6, 4.9 Hz, 1H), 7.64 (dd, J=7.6, 1.8 Hz, 1H), 8.11 (d, J=4.9 Hz, 1H), 8.51 (dd, J=4.9, 1.8 Hz, 1H)

2-(2-Aminopyrimidin-4-ylmethylthio)-N-(indazol-6-yl)pyridine-3-carboxamide (Compound No. 1-14)

¹H-NMR (400 MHz, DMSO-d$_6$)
δ 4.28 (s, 2H), 6.60-6.64 (m, 3H), 7.25 (dd, J=8.5, 1.4 Hz, 1H), 7.30 (dd, J=7.6, 4.9 Hz, 1H), 7.71 (d, J=8.5 Hz, 1H), 7.97-8.00 (m, 2H), 8.11 (d, J=4.9 Hz, 1H), 8.23 (s, 1H), 8.58 (dd, J=4.9, 1.6 Hz, 1H), 10.63 (s, 1H), 12.97 (s, 1H)

2-(2-Aminopyrimidin-4-ylmethylthio)-N-(4-n-propylphenyl)pyridine-3-carboxamide (Compound No. 1-15)

¹H-NMR (400 MHz, DMSO-d$_6$)
δ 0.88 (t, J=7.3 Hz, 3H), 1.55-1.60 (m, 2H), 2.50-2.54 (m, 2H), 4.26 (s, 2H), 6.60-6.63 (m, 3H), 7.17 (d, J=8.4 Hz, 2H), 7.27 (dd, J=7.6, 4.7 Hz, 1H), 7.60 (d, J=8.4 Hz, 2H) 7.93 (dd, J=7.6, 1.8 Hz, 1H), 8.11 (d, J=5.1 Hz, 1H), 8.56 (dd, J=4.7, 1.8 Hz, 1H), 10.41 (s, 1H)

2-(2-Aminopyrimidin-4-ylmethylthio)-N-(3,5-dimethylphenyl)benzamide (Compound No. 1-16)

$^1$H-NMR (400 MHz, DMSO-d$_6$)

δ 2.25 (s, 6H), 4.06 (s, 2H), 6.60-6.63 (m, 3H), 6.74 (s, 1H), 7.27 (td, J=7.3, 1.0 Hz, 1H), 7.35 (s, 2H), 7.42 (td, J=7.3, 1.5 Hz, 1H), 7.47-7.51 (m, 2H), 8.13 (d, J=4.9 Hz, 1H), 10.21 (s, 1H)

2-(2-Aminopyrimidin-4-ylmethylthio)-N-(4-chlorophenyl)benzamide (Compound No. 1-17)

$^1$H-NMR (400 MHz, DMSO-d$_6$)

δ 4.07 (s, 2H), 6.60-6.63 (m, 3H), 7.29 (td, J=7.5, 1.0 Hz, 1H), 7.40 (d, J=8.8 Hz, 2H), 7.45 (m, 1H), 7.52 (m, 2H), 7.75 (d, J=8.8 Hz, 2H), 8.12 (d, J=4.9 Hz, 1H), 10.51 (s, 1H)

[2-(2-Aminopyrimidin-4-ylmethylthio)phenyl]morpholinomethanone (Compound No. 1-18)

$^1$H-NMR (400 MHz, DMSO-d$_6$)

δ 2.98-3.05 (m, 2H), 3.46-3.48 (m, 2H), 3.57-3.66 (m, 4H), 4.06 (s, 2H), 6.52 (d, J=4.8 Hz, 1H), 6.64 (s, 2H), 7.21 (dd, J=7.6, 1.4 Hz, 1H), 7.27 (td, J=7.3, 1.2 Hz, 1H), 7.36 (td, J=7.3, 1.2 Hz, 1H), 7.50 (d, J=7.3 Hz, 1H), 8.12 (d, J=4.8 Hz, 1H)

2-(2-Aminopyrimidin-4-ylmethylthio)-N-(4'-methoxyphenethyl)benzamide (Compound No. 1-19)

$^1$H-NMR (400 MHz, DMSO-d$_6$)

δ 2.76 (t, J=7.3 Hz, 2H), 3.36-3.41 (m, 2H), 3.72 (s, 3H), 4.01 (s, 2H), 6.60 (d, J=4.9 Hz, 1H), 6.64 (s, 2H), 6.85 (dd, J=6.7, 2.1 Hz, 2H), 7.15-7.21 (m, 3H), 7.30-7.37 (m, 2H), 7.41 (d, J=7.4 Hz, 1H), 8.13 (d, J=4.9 Hz, 1H), 8.39 (t, J=5.6 Hz, 1H)

3-(2-Aminopyrimidin-4-ylmethylthio)-N-(3,5-dimethylphenyl)thiophene-2-carboxamide (Compound No. 1-20)

$^1$H-NMR (500 MHz, DMSO-d$_6$)

δ 2.26 (s, 6H), 4.09 (s, 2H), 6.55 (d, J=4.9 Hz, 1H), 6.60 (s, 2H), 6.75 (s, 1H), 7.25-7.28 (m, 3H), 7.82 (d, J=5.2 Hz, 1H), 8.13 (d, J=5.2 Hz, 1H), 9.89 (s, 1H)

[3-(2-Aminopyrimidin-4-ylmethylthio)thiophen-2-yl]morpholinomethanone (Compound No. 1-21)

$^1$H-NMR (400 MHz, CDCl$_3$)

δ 3.39 (br s, 4H), 3.52-3.58 (m, 4H), 4.02 (s, 2H), 6.48 (d, J=4.8 Hz, 1H), 6.63 (s, 2H), 7.21 (d, J=5.2 Hz, 1H), 7.73 (d, J=5.2 Hz, 1H), 8.12 (d, J=4.8 Hz, 1H)

N-(3,5-Dimethylphenyl)-2-(pyrimidin-4-ylmethylthio)pyridine-3-carboxamide (Compound No. 1-22)

$^1$H-NMR (400 MHz, DMSO-d$_6$)

δ 2.26 (s, 6H), 4.51 (s, 2H), 6.77 (s, 1H), 7.28 (dd, J=7.6, 4.6 Hz, 1H), 7.33 (s, 2H), 7.59 (dd, J=5.1, 1.2 Hz, 1H), 7.94 (dd, J=7.6, 1.7 Hz, 1H), 8.54 (dd, J=4.6, 1.7 Hz, 1H), 8.69 (d, J=5.1 Hz, 1H), 9.08 (d, J=1.2 Hz, 1H), 10.31 (s, 1H)

N-(4-Chlorophenyl)-2-(pyrimidin-4-ylmethylthio)pyridine-3-carboxamide (Compound No. 1-23)

$^1$H-NMR (400 MHz, DMSO-d$_6$)

δ 4.51 (s, 2H), 7.29 (dd, J=7.6, 4.6 Hz, 1H), 7.43 (d, J=8.8 Hz, 2H), 7.59 (dd, J=5.1, 1.5 Hz, 1H), 7.73 (d, J=8.8 Hz, 2H), 7.99 (dd, J=7.6, 1.7 Hz, 1H), 8.55 (dd, J=4.6, 1.7 Hz, 1H), 8.68 (d, J=5.1 Hz, 1H), 9.07 (d, J=1.5 Hz, 1H), 10.62 (s, 1H)

N-(Indan-5-yl)-2-(pyrimidin-4-ylmethylthio)pyridine-3-carboxamide (Compound No. 1-24)

$^1$H-NMR (400 MHz, DMSO-d$_6$)

δ 1.98-2.05 (m, 2H), 2.81-2.88 (m, 4H), 4.50 (s, 2H), 7.18 (d, J=8.1 Hz, 1H), 7.29 (m, 1H), 7.39 (m, 1H), 7.58-7.62 (m, 2H), 7.95 (dd, J=7.6, 1.7 Hz, 1H), 8.53 (dd, J=4.9, 1.7 Hz, 1H), 8.69 (d, J=5.4 Hz, 1H), 9.07 (d, J=1.2 Hz, 1H), 10.37 (s, 1H)

N-(4-tert-Butylphenyl)-2-(pyrimidin-4-ylmethylthio)pyridine-3-carboxamide (Compound No. 1-25)

$^1$H-NMR (400 MHz, DMSO-d$_6$)

δ 1.28 (s, 9H), 4.50 (s, 2H), 7.28 (dd, J=7.6, 4.9 Hz, 1H), 7.37 (dd, J=6.8, 2.0 Hz, 2H), 7.57-7.62 (m, 3H), 7.96 (dd, J=7.6, 1.7 Hz, 1H), 8.54 (dd, J=4.9, 1.7 Hz, 1H), 8.69 (d, J=5.1 Hz, 1H), 9.08 (d, J=1.2 Hz, 1H), 10.42 (s, 1H)

N-(3,5-Dimethylphenyl)-2-(2-methylthiopyrimidin-4-ylmethyl thio)pyridine-3-carboxamide (Compound No. 1-26)

$^1$H-NMR (400 MHz, CDCl$_3$)

δ 2.33 (d, J=0.5 Hz, 6H), 2.53 (s, 3H), 4.54 (s, 2H), 6.83 (s, 1H), 7.10 (d, J=5.1 Hz, 1H), 7.15 (dd, J=7.6, 4.9 Hz, 1H), 7.27 (s, 2H), 7.93 (dd, J=7.6, 1.7 Hz, 1H), 8.01 (s, 1H), 8.39 (d, J=5.1 Hz, 1H), 8.50 (dd, J=4.9, 1.7 Hz, 1H)

N-(3,5-Dimethylphenyl)-2-(2-methylsulfinylpyrimidin-4-ylmethylthio)pyridine-3-carboxamide (Compound No. 1-27)

$^1$H-NMR (500 MHz, DMSO-d$_6$)

δ 2.26 (s, 6H), 2.84 (s, 3H), 4.58 (s, 2H), 6.77 (s, 1H), 7.29 (dd, J=7.6, 4.9 Hz, 1H), 7.33 (s, 2H), 7.71 (d, J=5.2 Hz, 1H), 7.98 (dd, J=7.6, 1.8 Hz, 1H), 8.53 (dd, J=4.9, 1.8 Hz, 1H), 8.87 (d, J=5.2 Hz, 1H), 10.33 (s, 1H)

N-(4-Chlorophenyl)-2-(2-methylsulfinylpyrimidin-4-ylmethyl thio)pyridine-3-carboxamide (Compound No. 1-28)

$^1$H-NMR (400 MHz, DMSO-d$_6$)

δ 2.84 (s, 3H), 4.59 (s, 2H), 7.31 (dd, J=7.6, 4.9 Hz, 1H), 7.43 (d, J=8.8 Hz, 2H), 7.71 (d, J=5.1 Hz, 1H), 7.74 (d, J=8.8 Hz, 2H), 8.03 (dd, J=7.6, 1.7 Hz, 1H), 8.55 (dd, J=4.9, 1.7 Hz, 1H), 8.86 (d, J=5.1 Hz, 1H), 10.63 (s, 1H)

2-(2-Methylsulfinylpyrimidin-4-ylmethylthio)-N-(4-trifluoromethoxyphenyl)pyridine-3-carboxamide (Compound No. 1-29)

¹H-NMR (500 MHz, DMSO-d₆)

δ 2.84 (s, 3H), 4.59 (s, 2H), 7.32 (dd, J=7.6, 4.9 Hz, 1H), 7.39 (d, J=8.2 Hz, 2H), 7.71 (d, J=4.9 Hz, 1H), 7.82 (d, J=8.2 Hz, 2H), 8.04 (dd, J=7.6, 1.8 Hz, 1H), 8.55 (dd, J=4.9, 1.8 Hz, 1H), 8.87 (d, J=4.9 Hz, 1H), 10.68 (s, 1H)

N-(Isoquinolin-3-yl)-2-(2-methylsulfinylpyrimidin-4-ylmethylthio)pyridine-3-carboxamide (Compound No. 1-30)

¹H-NMR (500 MHz, DMSO-d₆)

δ 2.84 (s, 3H), 4.60 (s, 2H), 7.29 (dd, J=7.6, 4.9 Hz, 1H), 7.59 (t, J=7.6 Hz, 1H), 7.73 (d, J=5.2 Hz, 1H), 7.76 (t, J=7.6 Hz, 1H), 7.99 (d, J=7.6 Hz, 1H), 8.08-8.13 (m, 2H), 8.55 (dd, J=4.9, 1.5 Hz, 1H), 8.60 (s, 1H), 8.87 (d, J=5.2 Hz, 1H), 9.20 (s, 1H), 11.19 (s, 1H)

N-(3-Chlorophenyl)-2-(2-methylsulfinylpyrimidin-4-ylmethyl thio)pyridine-3-carboxamide (Compound No. 1-31)

¹H-NMR (500 MHz, DMSO-d₆)

δ 2.84 (s, 3H), 4.60 (s, 2H), 7.20 (m, 1H), 7.32 (dd, J=7.6, 4.9 Hz, 1H), 7.40 (m, 1H), 7.60 (m, 1H), 7.71 (d, J=5.2 Hz, 1H), 7.90 (m, 1H), 8.04 (dd, J=7.6, 1.8 Hz, 1H), 8.55 (dd, J=4.9, 1.8 Hz, 1H), 8.87 (d, J=5.2 Hz, 1H), 10.67 (s, 1H)

2-(2-Methylsulfinylpyrimidin-4-ylmethylthio)-N-(3-trifluoromethylphenyl)pyridine-3-carboxamide (Compound No. 1-32)

¹H-NMR (500 MHz, DMSO-d₆)

δ 2.84 (s, 3H), 4.60 (s, 2H), 7.33 (dd, J=7.6, 4.9 Hz, 1H), 7.49 (d, J=7.6 Hz, 1H), 7.62 (dd, J=7.9, 7.6 Hz, 1H), 7.72 (d, J=5.2 Hz, 1H) 7.93 (d, J=7.9 Hz, 1H), 8.08 (dd, J=7.6, 1.8 Hz, 1H), 8.19 (s, 1H), 8.56 (dd, J=4.9, 1.8 Hz, 1H), 8.87 (d, J=5.2 Hz, 1H), 10.81 (s, 1H)

N-(3,5-Dimethylphenyl)-2-(2-methylaminopyrimidin-4-ylmethylthio)pyridine-3-carboxamide (Compound No. 1-33)

¹H-NMR (500 MHz, DMSO-d₆)

δ 2.26 (s, 6H), 2.76 (d, J=4.6 Hz, 3H), 4.28 (s, 2H), 6.61 (d, J=4.9 Hz, 1H), 6.76 (s, 1H), 7.04 (d, J=4.3 Hz, 1H) 7.29 (dd, J=7.6, 4.9 Hz, 1H), 7.33 (s, 2H), 7.92 (dd, J=7.6, 1.6 Hz, 1H), 8.15 (s, 1H), 8.56 (dd, J=4.9, 1.6 Hz, 1H), 10.32 (s, 1H)

2-(2-Dimethylaminopyrimidin-4-ylmethylthio)-N-(3,5-dimethylphenyl)pyridine-3-carboxamide (Compound No. 1-34)

¹H-NMR (400 MHz, CDCl₃)

δ 2.32 (s, 6H), 3.12 (s, 6H), 4.46 (s, 2H), 6.55 (d, J=5.0 Hz, 1H), 6.81 (s, 1H), 7.15 (dd, J=7.6, 4.8 Hz, 1H), 7.23 (s, 2H), 7.96 (dd, J=7.6, 1.8 Hz, 1H), 8.14 (s, 1H), 8.20 (d, J=5.0 Hz, 1H), 8.53 (dd, J=4.8, 1.8 Hz, 1H)

Example 2

2-(2-Acetylaminopyrimidin-4-ylmethylthio)-N-(3,5-dimethylphenyl)pyridine-3-carboxamide (Compound No. 2-1)

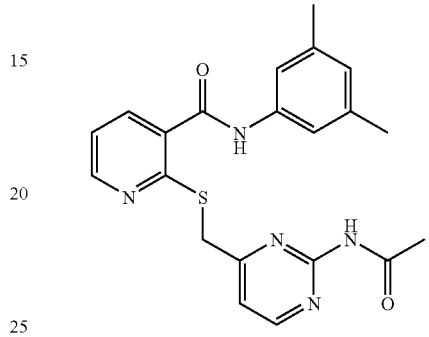

Triethylamine (45 μL, 0.32 mmol) was added to a solution of N-(3,5-dimethylphenyl)-2-thioxo-1,2-dihydropyridine-3-carboxamide (28 mg, 0.11 mmol, Reference Compound No. 13-1) and 2-acetylamino-4-(chloromethyl)pyrimidine (18 mg, 0.10 mmol, Reference Compound No. 11-1) in anhydrous N,N-dimethylformamide (1.0 mL) at room temperature, and the mixture was stirred for 16 hours. Ethyl acetate (30 mL) was added thereto, then the whole was washed with saturated aqueous sodium hydrogen carbonate solution (30 mL) and brine (30 mL), and the organic layer was dried over anhydrous magnesium sulfate. The solvent was evaporated under reduced pressure, and then the precipitated solid was filtered off with diethyl ether and washed. The solid was dried at 50° C. under reduced pressure to give 21 mg of the target compound as a light orange solid (Yield: 52%).

¹H-NMR (400 MHz, DMSO-d₆)

δ 2.16 (s, 3H), 2.26 (s, 6H), 4.43 (s, 2H), 6.77 (s, 1H), 7.21 (d, J=5.1 Hz, 1H), 7.28 (dd, J=7.6, 4.9 Hz, 1H), 7.33 (s, 2H), 7.95 (dd, J=7.6, 1.7 Hz, 1H), 8.52 (d, J=4.9 Hz, 1H), 8.54 (dd, J=4.9, 1.7 Hz, 1H), 10.33 (s, 1H), 10.49 (s, 1H)

As described below, Compounds Nos. 2-2 to 2-4 were obtained following the method similar to that of Compound No. 2-1, using the corresponding compounds selected from Reference Compounds Nos. 13-2 to 13-4, compounds which are on the market or compounds which are commonly known.

2-(2-Acetylaminopyrimidin-4-ylmethylthio)-N-(4-chlorophenyl)pyridine-3-carboxamide (Compound No. 2-2)

¹H-NMR (400 MHz, DMSO-d₆)

δ 2.15 (s, 3H), 4.44 (s, 2H), 7.21 (d, J=5.1 Hz, 1H), 7.30 (dd, J=7.6, 4.9 Hz, 1H), 7.43 (d, J=8.9 Hz, 2H), 7.74 (d, J=8.9 Hz, 2H), 8.00 (dd, J=7.6, 1.7 Hz, 1H), 8.51 (d, J=5.1 Hz, 1H), 8.56 (dd, J=4.9, 1.7 Hz, 1H), 10.49 (s, 1H), 10.62 (s, 1H)

2-(2-Acetylaminopyrimidin-4-ylmethylthio)-N-(4-trifluoromethoxyphenyl)pyridine-3-carboxamide (Compound No. 2-3)

¹H-NMR (400 MHz, DMSO-d₆)

δ 2.15 (s, 3H), 4.44 (s, 2H), 7.22 (d, J=5.1 Hz, 1H), 7.31 (dd, J=7.6, 4.9 Hz, 1H), 7.38 (d, J=8.7 Hz, 2H), 7.82 (d, J=8.7 Hz, 2H), 8.01 (dd, J=7.6, 1.7 Hz, 1H), 8.52 (d, J=4.9 Hz, 1H), 8.56 (dd, J=4.9, 1.7 Hz, 1H), 10.49 (s, 1H), 10.68 (s, 1H)

2-(2-Acetylaminopyrimidin-4-ylmethylthio)-N-(indan-5-yl)pyridine-3-carboxamide (Compound No. 2-4)

¹H-NMR (400 MHz, DMSO-d₆)

δ 1.97-2.04 (m, 2H), 2.15 (s, 3H), 2.80-2.88 (m, 4H), 4.43 (s, 2H), 7.18 (d, J=8.2 Hz, 1H), 7.21 (d, J=5.1 Hz, 1H), 7.28 (dd, J=7.6, 4.9 Hz, 1H), 7.39 (d, J=8.2 Hz, 1H), 7.62 (s, 1H), 7.95 (dd, J=7.6, 1H), 8.51 (d, J=5.1 Hz, 1H), 8.54 (dd, J=4.9, 1.7 Hz, 1H), 10.37 (s, 1H), 10.49 (s, 1H)

Example 3

2-(2-Diacetylaminopyrimidin-4-ylmethylthio)-N-(3,5-dimethylphenyl)pyridine-3-carboxamide (Compound No. 3-1)

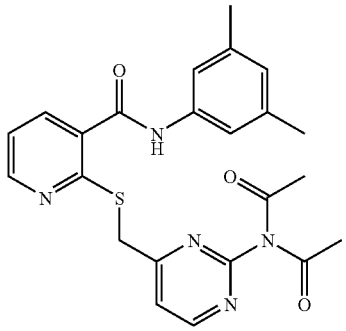

2-(2-Aminopyrimidin-4-ylmethylthio)-N-(3,5-dimethylphenyl)pyridine-3-carboxamide (2.0 g, 5.5 mmol, Compound No. 1-1) was suspended in acetic anhydride (20 mL), and the mixture was stirred for 4 hours at 100° C. The reaction mixture was diluted with ethyl acetate (1.0 L), washed with water (1.0 L), and dried over anhydrous magnesium sulfate. The solvent was evaporated under reduced pressure, and the residue was purified by silica gel column chromatography to give 0.69 g of the target compound as a pale yellow solid (Yield: 30%).

¹H-NMR (400 MHz, CDCl₃)

δ 2.17 (s, 6H), 2.32 (s, 6H), 4.60 (s, 2H), 6.82 (d, J=0.7 Hz, 1H), 7.14 (dd, J=7.6, 4.9 Hz, 1H), 7.25-7.27 (m, 2H), 7.53 (d, J=5.2 Hz, 1H), 7.87 (dd, J=7.6, 1.7 Hz, 1H), 8.08 (s, 1H), 8.46 (dd, J=4.9, 1.7 Hz, 1H), 8.69 (d, J=5.2 Hz, 1H)

As described below, Compound No. 3-2 was obtained following the method similar to that of Compound No. 3-1, using the corresponding compounds selected from Compound No. 1-4, compounds which are on the market or compounds which are commonly known.

2-(2-Diacetylaminopyrimidin-4-ylmethylthio)-N-(indan-5-yl)pyridine-3-carboxamide (Compound No. 3-2)

¹H-NMR (400 MHz, CDCl₃)

δ 2.04-2.12 (m, 2H), 2.23 (s, 6H), 2.86-2.92 (m, 4H), 4.59 (s, 2H), 7.14 (dd, J=7.6, 4.9 Hz, 1H), 7.20 (d, J=7.8 Hz, 1H), 7.53 (d, J=5.1 Hz, 1H), 7.57 (s, 1H), 7.88 (d, J=7.8 Hz, 1H) 8.05 (s, 1H), 8.46 (dd, J=4.9, 1.7 Hz, 1H), 8.69 (d, J=5.1 Hz, 1H), 8.89 (s, 1H)

Example 4

2-(2-Cyclopropylaminopyrimidin-4-ylmethylthio)-N-(3,5-dimethylphenyl)pyridine-3-carboxamide (Compound No. 4-1)

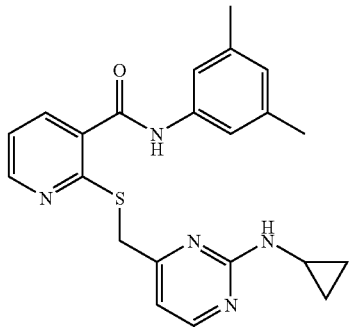

Cyclopropylamine (6.0 mL) was added to N-(3,5-dimethylphenyl)-2-(2-methylsulfinylpyrimidin-4-ylmethylthio)pyridine-3-carboxamide (990 mg, 2.4 mmol, Compound No. 1-27), and the mixture was stirred for 30 minutes at 80° C. The reaction mixture was diluted with ethyl acetate (80 mL), washed twice with water (50 mL), and dried over anhydrous magnesium sulfate. The solvent was evaporated under reduced pressure, then the residue was purified by silica gel column chromatography to give 650 mg (recrystallized from ethanol) of the target compound as a colorless solid (Yield: 67%).

¹H-NMR (500 MHz, DMSO-d₆)

δ 0.40-0.45 (m, 2H), 0.55-0.65 (m, 2H), 2.26 (s, 6H), 2.67 (m, 1H), 4.29 (s, 2H), 6.66 (d, J=5.2 Hz, 1H), 6.76 (s, 1H), 7.27 (dd, J=7.6, 4.9 Hz, 1H), 7.30-7.35 (m, 3H), 7.92 (dd, J=7.6, 1.8 Hz, 1H), 8.19 (d, J=5.2 Hz, 1H), 8.56 (dd, J=4.9, 1.8 Hz, 1H), 10.32 (s, 1H)

As described below, Compounds Nos. 4-2 to 4-36 were obtained following the method similar to that of Compound No. 4-1, using the corresponding compounds selected from Compounds Nos. 1-27 to 1-32, compounds which are on the market or compounds which are commonly known.

N-(4-Chlorophenyl)-2-(2-morpholinopyrimidin-4-ylmethylthio)pyridine-3-carboxamide (Compound No. 4-2)

¹H-NMR (400 MHz, DMSO-d₆)

δ 3.60-3.66 (m, 8H), 4.33 (s, 2H), 6.71 (d, J=5.1 Hz, 1H), 7.29 (dd, J=7.6, 4.9 Hz, 1H), 7.42 (d, J=8.8 Hz, 2H), 7.73 (d, J=8.8 Hz, 2H), 7.99 (dd, J=7.6, 1.7 Hz, 1H), 8.26 (d, J=5.1 Hz, 1H), 8.57 (dd, J=4.9, 1.7 Hz, 1H), 10.61 (s, 1H)

2-(2-Morpholinopyrimidin-4-ylmethylthio)-N-(4-trifluoromethoxyphenyl)pyridine-3-carboxamide (Compound No. 4-3).

$^1$H-NMR (400 MHz, DMSO-d$_6$)
δ 3.61-3.65 (m, 8H), 4.34 (s, 2H), 6.72 (d, J=4.9 Hz, 1H), 7.31 (dd, J=7.6, 4.9 Hz, 1H), 7.38 (d, J=8.7 Hz, 2H), 7.81 (d, J=8.7 Hz, 2H), 7.99 (dd, J=7.6, 1.7 Hz, 1H), 8.27 (d, J=4.9 Hz, 1H), 8.58 (dd, J=4.9, 1.7 Hz, 1H), 10.68 (s, 1H)

N-(3,5-Dimethylphenyl)-2-(2-morpholinopyrimidin-4-ylmethyl thio)pyridine-3-carboxamide (Compound No. 4-4)

$^1$H-NMR (400 MHz, DMSO-d$_6$)
δ 2.26 (s, 6H), 3.61-3.66 (m, 8H), 4.33 (s, 2H), 6.71 (d, J=4.9 Hz, 1H), 6.77 (s, 1H), 7.28 (dd, J=7.6, 4.9 Hz, 1H), 7.33 (s, 2H), 7.93 (dd, J=7.6, 1.7 Hz, 1H), 8.27 (d, J=4.9 Hz, 1H), 8.56 (dd, J=4.9, 1.7 Hz, 1H), 10.32 (s, 1H)

N-(4-Chlorophenyl)-2-(2-cyclopropylaminopyrimidin-4-ylmethylthio)pyridine-3-carboxamide (Compound No. 4-5)

$^1$H-NMR (400 MHz, DMSO-d$_6$)
δ 0.40-0.45 (m, 2H), 0.59-0.64 (m, 2H), 2.67 (m, 1H), 4.29 (s, 2H), 6.66 (d, J=4.9 Hz, 1H), 7.29 (dd, J=7.6, 4.9 Hz, 1H), 7.35 (m, 1H), 7.42 (d, J=8.8 Hz, 2H), 7.73 (d, J=8.8 Hz, 2H), 7.97 (dd, J=7.6, 1.7 Hz, 1H), 8.19 (d, J=4.9 Hz, 1H), 8.57 (dd, J=4.9, 1.7 Hz, 1H), 10.62 (s, 1H)

2-(2-Cyclopropylaminopyrimidin-4-ylmethylthio)-N-(4-trifluoromethoxyphenyl)pyridine-3-carboxamide (Compound No. 4-6)

$^1$H-NMR (400 MHz, DMSO-d$_6$)
δ 0.40-0.45 (m, 2H), 0.58-0.64 (m, 2H), 2.67 (m, 1H), 4.29 (s, 2H), 6.66 (d, J=4.9 Hz, 1H), 7.30 (dd, J=7.6, 4.9 Hz, 1H), 7.35 (m, 1H), 7.38 (d, J=8.7 Hz, 2H), 7.81 (d, J=8.7 Hz, 2H), 7.98 (dd, J=7.6, 1.7 Hz, 1H), 8.19 (d, J=4.9 Hz, 1H), 8.58 (dd, J=4.9, 1.7 Hz, 1H), 10.68 (s, 1H)

2-(2-Cyclopropylaminopyrimidin-4-ylmethylthio)-N-(isoquinolin-3-yl)pyridine-3-carboxamide (Compound No. 4-7)

$^1$H-NMR (400 MHz, DMSO-d$_6$)
δ 0.40-0.44 (m, 2H), 0.58-0.64 (m, 2H), 2.67 (m, 1H), 4.31 (s, 2H), 6.68 (d, J=4.9 Hz, 1H), 7.27 (dd, J=7.6, 4.9 Hz, 1H), 7.36 (br s, 1H), 7.58 (ddd, J=8.1, 7.8, 1.2 Hz, 1H), 7.75 (ddd, J=8.1, 7.3, 1.2 Hz, 1H), 7.98 (d, J=7.8 Hz, 1H), 8.05 (dd, J=7.6, 1.7 Hz, 1H), 8.10 (d, J=7.3 Hz, 1H), 8.19 (d, J=4.9 Hz, 1H), 8.57 (dd, J=4.9, 1.7 Hz, 1H), 8.60 (br s, 1H), 9.20 (s, 1H), 11.18 (s, 1H)

N-(3-Chlorophenyl)-2-(2-cyclopropylaminopyrimidin-4-ylmethylthio)pyridine-3-carboxamide (Compound No. 4-8)

$^1$H-NMR (400 MHz, DMSO-d$_6$)
δ 0.40-0.45 (m, 2H), 0.59-0.64 (m, 2H), 2.67 (m, 1H), 4.30 (s, 2H), 6.66 (d, J=4.9 Hz, 1H), 7.20 (ddd, J=8.1, 7.1, 2.0 Hz, 1H), 7.30 (dd, J=7.6, 4.9 Hz, 1H), 7.36 (m, 1H), 7.39 (dd, J=8.3, 8.1 Hz, 1H), 7.59 (d, J=8.3 Hz, 1H), 7.90 (t, J=2.0 Hz, 1H), 7.99 (dd, J=7.6, 1.7 Hz, 1H), 8.19 (d, J=4.9 Hz, 1H), 8.58 (dd, J=4.9, 1.7 Hz, 1H), 10.67 (s, 1H)

2-(2-Cyclopropylaminopyrimidin-4-ylmethylthio)-N-(3-trifluoromethylphenyl)pyridine-3-carboxamide (Compound No. 4-9)

$^1$H-NMR (500 MHz, DMSO-d$_6$)
δ 0.41-0.45 (m, 2H), 0.59-0.63 (m, 2H), 2.67 (m, 1H), 4.30 (s, 2H), 6.67 (d, J=4.9 Hz, 1H), 7.31 (dd, J=7.6, 4.9 Hz, 1H), 7.33 (m, 1H), 7.48 (d, J=7.6 Hz, 1H), 7.61 (dd, J=1.9, 1.9 Hz, 1H), 7.92 (d, J=8.6 Hz, 1H), 8.03 (dd, J=7.6, 1.8 Hz, 1H), 8.18-8.19 (m, 2H), 8.59 (dd, J=4.9, 1.8 Hz, 1H), 10.81 (s, 1H)

2-(2-n-Butylaminopyrimidin-4-ylmethylthio)-N-(3,5-dimethyl phenyl)pyridine-3-carboxamide (Compound No. 4-10)

$^1$H-NMR (500 MHz, DMSO-d$_6$)
δ 0.86 (t, J=7.3 Hz, 3H), 1.25-1.33 (m, 2H), 1.43-1.50 (m, 2H), 2.26 (s, 6H), 3.19-3.24 (m, 2H), 4.27 (s, 2H), 6.59 (d, J=4.9 Hz, 1H) 6.76 (s, 01H), 7.12 (br s, 1H), 7.27 (dd, J=7.6, 4.9 Hz, 1H), 7.33 (s, 2H), 7.92 (dd, J=7.6, 1.8 Hz, 1H), 8.14 (d, J=4.9 Hz, 1H), 8.55 (dd, J=4.9, 1.8 Hz, 1H), 10.32 (s, 1H)

2-(2-n-Butylaminopyrimidin-4-ylmethylthio)-N-(4-chlorophenyl)pyridine-3-carboxamide (Compound No. 4-11)

$^1$H-NMR (500 MHz, DMSO-d$_6$)
δ 0.86 (t, J=7.3 Hz, 3H), 1.24-1.33 (m, 2H), 1.43-1.49 (m, 2H), 3.18-3.23 (m, 2H), 4.28 (s, 2H), 6.59 (d, J=5.2 Hz, 1H), 7.12 (br s, 1H), 7.29 (dd, J=7.6, 4.9 Hz, 1H), 7.42 (d, J=8.6 Hz, 2H), 7.74 (d, J=8.6 Hz, 2H), 7.97 (dd, J=7.6, 1.8 Hz, 1H), 8.14 (d, J=5.2 Hz, 1H), 8.57 (dd, J=4.9, 1.8 Hz, 1H), 10.61 (s, 1H)

2-(2-n-Butylaminopyrimidin-4-ylmethylthio)-N-(4-trifluoromethoxyphenyl)pyridine-3-carboxamide (Compound No. 4-12)

$^1$H-NMR (500 MHz, DMSO-d$_6$)
δ 0.85 (t, J=7.3 Hz, 3H), 1.24-1.32 (m, 2H), 1.42-1.49 (m, 2H), 3.18-3.23 (m, 2H), 4.28 (s, 2H), 6.59 (d, J=5.2 Hz, 1H), 7.11 (br s, 1H), 7.30 (dd, J=7.6, 4.9 Hz, 1H), 7.38 (d, J=8.7 Hz, 2H), 7.82 (d, J=8.7 Hz, 2H), 7.98 (dd, J=7.6, 1.8 Hz, 1H), 8.14 (d, J=5.2 Hz, 1H), 8.58 (dd, J=4.9, 1.8 Hz, 1H), 10.68 (s, 1H)

2-(2-Cyclobutylaminopyrimidin-4-ylmethylthio)-N-(isoquinolin-3-yl)pyridine-3-carboxamide (Compound No. 4-13)

$^1$H-NMR (400 MHz, DMSO-d$_6$)
δ 1.50-1.65 (m, 2H), 1.85-2.00 (m, 2H), 2.15-2.20 (m, 2H), 4.28 (s, 2H), 4.29 (m, 1H), 6.61 (d, J=4.9 Hz, 1H), 7.31 (dd, J=7.8, 4.9 Hz, 1H), 7.43-7.50 (m, 2H), 7.61 (t, J=7.8 Hz, 1H), 7.93 (d, J=8.3 Hz, 1H), 8.02 (dd, J=7.8, 1.7 Hz, 1H), 8.14 (d, J=4.9 Hz, 1H), 8.19 (s, 1H), 8.59 (dd, J=4.9, 1.7 Hz, 1H), 10.81 (s, 1H)

N-(3-Chlorophenyl)-2-(2-cyclobutylaminopyrimidin-4-ylmethylthio)pyridine-3-carboxamide (Compound No. 4-14)

$^1$H-NMR (400 MHz, DMSO-d$_6$)
δ 1.56-1.65 (m, 2H), 1.88-1.99 (m, 2H), 2.14-2.21 (m, 2H), 4.28 (s, 2H), 4.29 (m, 1H), 6.61 (d, J=4.9 Hz, 1H), 7.19 (m, 1H), 7.30 (dd, J=7.6, 4.9 Hz, 1H), 7.37-7.42 (m, 2H), 7.60 (d,

J=8.3 Hz, 1H), 7.90 (s, 1H), 7.98 (dd, J=7.6, 1.7 Hz, 1H), 8.14 (d, J=4.9 Hz, 1H), 8.58 (dd, J=4.9, 1.7 Hz, 1H), 10.66 (s, 1H)

2-[2-(4-Acetylpiperazin-1-yl)pyrimidin-4-ylmethylthio]-N-(3,5-dimethylphenyl)pyridine-3-carboxamide (Compound No. 4-15)

$^1$H-NMR (400 MHz, DMSO-$d_6$)

δ 2.03 (s, 3H), 2.26 (s, 6H), 3.42-3.49 (m, 4H), 3.64-3.68 (m, 2H), 3.72-3.75 (m, 2H), 4.33 (s, 2H), 6.71 (d, J=4.9 Hz, 1H), 6.77 (s, 1H), 7.28 (dd, J=7.6, 4.9 Hz, 1H), 7.33 (s, 2H), 7.94 (dd, J=7.6, 1.7 Hz, 1H), 8.27 (d, J=4.9 Hz, 1H), 8.56 (dd, J=4.9, 1.7 Hz, 1H), 10.33 (s, 1H)

2-[2-(4-Acetylpiperazin-1-yl)pyrimidin-4-ylmethylthio]-N-(4-chlorophenyl)pyridine-3-carboxamide (Compound No. 4-16)

$^1$H-NMR (500 MHz, DMSO-$d_6$)

δ 2.03 (s, 3H), 3.46-3.50 (m, 4H), 3.64-3.67 (m, 2H), 3.72-3.75 (m, 2H), 4.34 (s, 2H), 6.71 (d, J=4.9 Hz, 1H), 7.30 (dd, J=7.6, 4.9 Hz, 1H), 7.42 (d, J=8.9 Hz, 2H), 7.74 (d, J=8.9 Hz, 2H), 7.89 (dd, J=7.6, 1.8 Hz, 1H), 8.27 (d, J=4.9 Hz, 1H), 8.58 (dd, J=4.9, 1.8 Hz, 1H), 10.62 (s, 1H)

2-[2-(4-Acetylpiperazin-1-yl)pyrimidin-4-ylmethylthio]-N-(4-trifluoromethoxyphenyl)pyridine-3-carboxamide (Compound No. 4-17)

$^1$H-NMR (500 MHz, DMSO-$d_6$)

δ 2.03 (s, 3H), 3.48-3.50 (m, 4H), 3.64-3.67 (m, 2H), 3.72-3.75 (m, 2H), 4.34 (s, 2H), 6.71 (d, J=4.9 Hz, 1H), 7.31 (dd, J=7.6, 4.9 Hz, 1H), 7.38 (d, J=8.9 Hz, 2H), 7.82 (d, J=8.9 Hz, 2H), 8.00 (dd, J=7.6, 1.8 Hz, 1H), 8.27 (d, J=4.9 Hz, 1H), 8.59 (dd, J=4.9, 1.8 Hz, 1H), 10.68 (s, 1H)

N-(3,5-Dimethylphenyl)-2-[2-(1-phenylethyl)aminopyrimidin-4-ylmethylthio]pyridine-3-carboxamide (Compound No. 4-18)

$^1$H-NMR (400 MHz, DMSO-$d_6$)

δ 1.40 (d, J=7.1 Hz, 3H), 2.26 (s, 6H), 4.27 (s, 2H), 5.07 (m, 1H), 6.59 (d, J=5.1 Hz, 1H), 6.77 (s, 1H), 7.13-7.16 (m, 1H), 7.22-7.38 (m, 7H), 7.69 (br s, 1H), 7.92 (dd, J=7.6, 1.7 Hz, 1H), 8.11 (d, J=5.1 Hz, 1H), 8.54 (dd, J=4.9, 1.7 Hz, 1H), 10.32 (s, 1H)

N-(3,5-Dimethylphenyl)-2-[2-(2-hydroxyethyl)aminopyrimidin-4-ylmethylthio]pyridine-3-carboxamide (Compound No. 4-19)

$^1$H-NMR (400 MHz, DMSO-$d_6$)

δ 2.26 (s, 6H), 3.27-3.31 (m, 2H), 3.38-3.50 (m, 2H), 4.27 (s, 2H), 4.65 (t, J=5.6 Hz, 1H), 6.62 (d, J=4.9 Hz, 1H), 6.77 (s, 1H), 7.00 (br s, 1H), 7.27 (dd, J=7.6, 4.9 Hz, 1H), 7.33 (s, 2H), 7.92 (dd, J=7.6, 1.7 Hz, 1H), 8.15 (d, J=4.9 Hz, 1H), 8.56 (dd, J=4.9, 1.7 Hz, 1H), 10.33 (s, 1H)

N-(3,5-Dimethylphenyl)-2-[2-(2-ethoxyethyl)aminopyrimidin-4-ylmethylthio]pyridine-3-carboxamide (Compound No. 4-20)

$^1$H-NMR (400 MHz, DMSO-$d_6$)

δ 1.07 (t, J=6.8 Hz, 3H), 2.26 (s, 6H), 3.30-3.50 (m, 6H), 4.28 (s, 2H), 6.62 (d, J=4.9 Hz, 1H), 6.76 (s, 1H), 7.06 (br s, 1H), 7.27 (dd, J=7.6, 4.9 Hz, 1H), 7.33 (s, 2H), 7.92 (dd, J=7.6, 1.7 Hz, 1H), 8.15 (d, J=4.9 Hz, 1H), 8.56 (dd, J=4.9, 1.7 Hz, 1H), 10.32 (s, 1H)

N-(3,5-Dimethylphenyl)-2-[2-(2-morpholinoethyl)aminopyrimidin-4-ylmethylthio]pyridine-3-carboxamidemonohydrochloride (Compound No. 4-21)

$^1$H-NMR (400 MHz, DMSO-$d_6$)

δ 2.26 (s, 6H), 3.27 (br s, 2H), 3.60-4.00 (m, 10H), 4.34 (s, 2H), 6.77 (d, J=4.9 Hz, 1H), 6.77 (s, 1H), 7.29 (dd, J=7.6, 4.9 Hz, 1H), 7.34 (s, 2H), 7.50 (br s, 1H), 7.95 (dd, J=7.6, 1.7 Hz, 1H), 8.25 (d, J=4.9 Hz, 1H), 8.56 (dd, J=4.9, 1.7 Hz, 1H), 10.20 (s, 1H), 10.36 (s, 1H)

2-[2-(2-Ethoxyethyl)aminopyrimidin-4-ylmethylthio]-N-(4-trifluoromethoxyphenyl)pyridine-3-carboxamide (Compound No. 4-22)

$^1$H-NMR (400 MHz, DMSO-$d_6$)

δ 1.07 (t, J=6.8 Hz, 3H), 3.30-3.50 (m, 6H), 4.29 (s, 2H), 6.63 (d, J=4.9 Hz, 1H), 7.07 (br s, 1H), 7.29 (dd, J=7.6, 4.9 Hz, 1H) 7.37 (d, J=8.3 Hz, 2H), 7.82 (d, J=8.3 Hz, 2H) 7.98 (dd, J=7.6, 1.7 Hz, 1H), 8.15 (d, J=4.9 Hz, 1H), 8.58 (dd, J=4.9, 1.7 Hz, 1H), 10.68 (s, 1H)

N-(4-Chlorophenyl)-2-[2-(2-morpholinoethyl)aminopyrimidin-4-ylmethylthio]pyridine-3-carboxamide (Compound No. 4-23)

$^1$H-NMR (400 MHz, DMSO-$d_6$)

δ 2.30-2.50 (m, 8H), 3.53 (br s, 4H), 4.28 (s, 2H), 6.62 (d, J=4.9 Hz, 1H), 6.95 (S, 1H), 7.29 (dd, J=7.6, 4.9 Hz, 1H), 7.42 (d, J=8.8 Hz, 2H), 7.74 (d, J=8.8 Hz, 2H), 7.98 (dd, J=7.6, 1.7 Hz, 1H), 8.15 (br s, 1H), 8.57 (dd, J=4.9, 1.7 Hz, 1H), 10.61 (br s, 1H)

N-(3,5-Dimethylphenyl)-2-[2-(1,4-trans-4-hydroxycyclohexyl amino)pyrimidin-4-ylmethylthio]pyridine-3-carboxamide (Compound No. 4-24)

$^1$H-NMR (400 MHz, DMSO-$d_6$)

δ 1.15-1.20 (m, 4H), 1.76-1.88 (m, 4H), 2.26 (s, 6H), 3.35 (m, 1H), 3.60 (m, 1H), 4.26 (s, 2H), 4.50 (d, J=4.3 Hz, 1H), 6.58 (d, J=5.2 Hz, 1H), 6.76 (s, 1H), 6.97 (br s, 1H), 7.27 (dd, J=7.6, 4.9 Hz, 1H), 7.33 (s, 2H), 7.92 (dd, J=7.6, 1.5 Hz, 1H), 8.14 (d, J=5.2 Hz, 1H), 8.56 (dd, J=4.9, 1.5 Hz, 1H), 10.31 (s, 1H)

N-(3,5-Dimethylphenyl)-2-[2-(4-(2-hydroxyethyl)piperazin-1-yl)pyrimidin-4-ylmethylthio]pyridine-3-carboxamide (Compound No. 4-25)

$^1$H-NMR (300 MHz, CDCl$_3$)

δ 2.32 (s, 6H), 2.54 (t, J=5.1 Hz, 4H), 2.58 (t, J=5.3 Hz, 2H), 3.66 (t, J=5.3 Hz, 2H), 3.81 (t, J=5.1 Hz, 4H), 4.44 (s, 2H), 6.61 (d, J=5.0 Hz, 1H), 6.81 (s, 1H), 7.15 (dd, J=7.7, 4.8 Hz, 1H), 7.23 (s, 2H), 7.95 (dd, J=7.7, 1.8 Hz, 1H), 8.05 (br s, 1H), 8.20 (d, J=5.0 Hz, 1H), 8.54 (dd, J=4.8, 1.8 Hz, 1H)

2-[2-(4-(2-Hydroxyethyl)piperazin-1-yl)pyrimidin-4-ylmethylthio]-N-(isoquinolin-3-yl)pyridine-3-carboxamide (Compound No. 4-26)

$^1$H-NMR (300 MHz, CDCl$_3$)

δ 2.50-2.65 (m, 6H), 3.66 (t, J=5.3 Hz, 2H), 3.83 (t, J=5.1 Hz, 4H), 4.45 (s, 2H), 6.64 (d, J=5.0 Hz, 1H), 7.16 (dd, J=7.7,

N-(3-Chlorophenyl)-2-[2-(4-(2-hydroxyethyl)piperazin-1-yl)pyrimidin-4-ylmethylthio]pyridine-3-carboxamide (Compound No. 4-27)

$^1$H-NMR (300 MHz, CDCl$_3$)

δ 2.53 (t, J=5.0 Hz, 4H), 2.58 (t, J=5.3 Hz, 2H), 3.66 (t, J=5.3 Hz, 2H), 3.79 (t, J=5.0 Hz, 4H), 4.46 (s, 2H), 6.60 (d, J=5.0 Hz, 1H), 7.10-7.20 (m, 2H), 7.28 (m, 1H), 7.45 (d, J=8.3 Hz, 1H), 7.71 (s, 1H), 7.99 (d, J=7.7 Hz, 1H), 8.21 (d, J=5.0 Hz, 1H), 8.31 (br s, 1H), 8.56 (d, J=4.8 Hz, 1H)

2-[2-(4-(2-Hydroxyethyl)piperazin-1-yl)pyrimidin-4-ylmethylthio]-N-(3-trifluoromethylphenyl)pyridine-3-carboxamide (Compound No. 4-28)

$^1$H-NMR (300 MHz, CDCl$_3$)

δ 2.53 (t, J=5.0 Hz, 4H), 2.58 (t, J=5.3 Hz, 2H), 3.66 (t, J=5.3 Hz, 2H), 3.79 (t, J=5.0 Hz, 4H), 4.47 (s, 2H), 6.61 (d, J=5.0 Hz, 1H), 7.19 (dd, J=7.7, 4.8 Hz, 1H), 7.43 (d, J=7.9 Hz, 1H), 7.49 (dd, J=8.1, 7.9 Hz, 1H), 7.82 (d, J=7.9 Hz, 1H), 7.87 (s, 1H), 8.01 (dd, J=7.7, 1.8 Hz, 1H), 8.21 (d, J=5.0 Hz, 1H), 8.45 (br s, 1H), 8.57 (dd, J=4.8, 1.8 Hz, 1H)

N-(3,5-Dimethylphenyl)-2-[2-(4-methylpiperazin-1-yl)pyrimidin-4-ylmethylthio]pyridine-3-carboxamide (Compound No. 4-29)

$^1$H-NMR (300 MHz, CDCl$_3$)

δ 2.32 (s, 6H), 2.33 (s, 3H), 2.40-2.50 (m, 4H), 3.76-3.88 (m, 4H), 4.44 (s, 2H), 6.60 (d, J=5.1 Hz, 1H), 6.81 (s, 1H), 7.15 (dd, J=7.7, 4.8 Hz, 1H), 7.23 (s, 2H), 7.95 (dd, J=7.7, 1.8 Hz, 1H), 8.06 (br s, 1H) 8.20 (d, J=5.0 Hz, 1H), 8.53 (dd, J=4.8, 1.8 Hz, 1H)

N-(Isoquinolin-3-yl)-2-[2-(4-methylpiperazin-1-yl)pyrimidin-4-ylmethylthio]pyridine-3-carboxamide (Compound No. 4-30)

$^1$H-NMR (300 MHz, CDCl$_3$)

δ 2.34 (s, 3H), 2.40-2.51 (m, 4H), 3.80-3.90 (m, 4H), 4.45 (s, 2H), 6.65 (d, J=5.0 Hz, 1H), 7.16 (dd, J=7.7, 5.0 Hz, 1H), 7.52 (dd, J=8.1, 7.2 Hz, 1H), 7.68 (dd, J=8.1, 7.2 Hz, 1H), 7.87 (d, J=8.1 Hz, 1H), 7.92 (d, J=8.1 Hz, 1H), 7.99 (dd, J=7.7, 1.8 Hz, 1H), 8.19 (d, J=5.0 Hz, 1H), 8.56 (dd, J=5.0, 1.8 Hz, 1H), 8.74 (s, 1H), 8.83 (br s, 1H), 8.99 (s, 1H)

N-(3-Chlorophenyl)-2-[2-(4-methylpiperazin-1-yl)pyrimidin-4-ylmethylthio]pyridine-3-carboxamide (Compound No. 4-31)

$^1$H-NMR (300 MHz, CDCl$_3$)

δ 2.34 (s, 3H), 2.44 (t, J=5.0 Hz, 4H), 3.80 (t, J=4.6 Hz, 4H), 4.46 (s, 2H), 6.59 (d, J=5.0 Hz, 1H), 7.13 (d, J=8.1 Hz, 1H), 7.18 (dd, J=7.7, 4.8 Hz, 1H), 7.30 (t, J=8.1 Hz, 1H), 7.44 (d, J=8.1 Hz, 1H), 7.72 (br s, 1H), 7.98 (dd, J=7.7, 1.8 Hz, 1H), 8.21 (d, J=5.0 Hz, 1H), 8.31 (br s, 1H), 8.56 (dd, J=4.8, 1.8 Hz, 1H)

4.8 Hz, 1H), 7.52 (dd, J=7.2, 7.0 Hz, 1H), 7.68 (dd, J=8.1, 7.0 Hz, 1H), 7.87 (d, J=8.4 Hz, 1H), 7.91 (d, J=8.6 Hz, 1H) 7.99 (dd, J=7.7, 1.8 Hz, 1H), 8.19 (d, J=5.0 Hz, 1H), 8.56 (dd, J=4.8, 1.8 Hz, 1H), 8.75 (s, 1H), 8.86 (s, 1H), 8.97 (s, 1H)

2-[2-(4-Methylpiperazin-1-yl)pyrimidin-4-ylmethylthio]-N-(3-trifluorophenyl)pyridine-3-carboxamide Hydrochloride (Compound No. 4-32)

$^1$H-NMR (300 MHz, CDCl$_3$)

δ 2.74 (br.s, 3H), 2.90-3.10 (m, 2H), 3.25-3.50 (m, 4H), 4.36 (s, 2H), 4.63 (br d, J=4.1 Hz, 2H), 6.81 (d, J=5.0 Hz, 1H), 7.30 (dd, J=7.7, 4.8 Hz, 1H), 7.47 (d, J=7.7 Hz, 1H), 7.60 (t, J=7.7 Hz, 1H), 7.94 (d, J=8.4 Hz, 1H), 8.07 (d, J=7.6 Hz, 1H), 8.21 (s, 1H), 8.32 (d, J=5.0 Hz, 1H), 8.58 (br d, J=4.8 Hz, 1H), 10.91 (s, 1H), 11.06 (br s, 1H)

N-(3,5-Dimethylphenyl)-2-[2-(piperazin-1-yl)pyrimidin-4-yl methylthio]pyridine-3-carboxamide (Compound No. 4-33)

$^1$H-NMR (300 MHz, CDCl$_3$)

δ 2.32 (s, 6H), 2.85-2.95 (m, 4H), 3.76-3.83 (m, 4H), 4.44 (s, 2H), 6.60 (d, J=5.0 Hz, 1H), 6.81 (s, 1H), 7.16 (dd, J=7.3, 5.0 Hz, 1H), 7.23 (s, 2H), 7.95 (dd, J=7.3, 1.8 Hz, 1H), 8.06 (br s, 1H), 8.19 (dd, J=5.0 Hz, 1H), 8.54 (dd, J=5.0, 1.8 Hz, 1H)

N-(Isoquinolin-3-yl)-2-[2-(piperazin-1-yl)pyrimidin-4-ylmethylthio]pyridine-3-carboxamide (Compound No. 4-34)

$^1$H-NMR (300 MHz, CDCl$_3$)

δ 2.91 (t, J=5.0 Hz, 4H), 3.80 (t, J=5.0 Hz, 4H), 4.45 (s, 2H), 6.65 (d, J=5.1 Hz, 1H), 7.14 (dd, J=7.7, 4.8 Hz, 1H), 7.52 (t, J=7.9 Hz, 1H), 7.70 (t, J=7.9 Hz, 1H), 7.86-7.90 (m, 2H) 7.99 (dd, J=7.7, 1.8 Hz, 1H), 8.19 (d, J=5.0 Hz, 1H), 8.55 (dd, J=4.8, 1.8 Hz, 1H), 8.77 (s, 1H), 8.86 (s, 1H), 9.27 (br s, 1H)

N-(3-Chlorophenyl)-2-[2-(piperazin-1-yl)pyrimidin-4-ylmethylthio]pyridine-3-carboxamide (Compound No. 4-35)

$^1$H-NMR (300 MHz, CDCl$_3$)

δ 2.92 (t, J=5.0 Hz, 4H), 3.79 (t, J=5.0 Hz, 4H), 4.45 (s, 2H), 6.59 (d, J=5.0 Hz, 1H), 7.14-7.21 (m, 2H), 7.28 (t, J=8.1 Hz, 1H), 7.44 (d, J=8.1 Hz, 1H), 7.71 (s, 1H), 7.98 (dd, J=7.5, 1.7 Hz, 1H), 8.20 (d, J=5.0 Hz, 1H), 8.31 (br s, 1H), 8.56 (dd, J=4.8, 1.7 Hz, 1H)

2-[2-(piperazin-1-yl)pyrimidin-4-ylmethylthio]-N-(3-trifluorophenyl)pyridine-3-carboxamide (Compound No. 4-36)

$^1$H-NMR (300 MHz, CDCl$_3$)

δ 2.84 (t, J=5.0 Hz, 4H), 3.72 (t, J=5.0 Hz, 4H), 4.45 (s, 2H), 6.58 (d, J=5.0 Hz, 1H), 7.16 (dd, J=7.7, 4.8 Hz, 1H), 7.40 (d, J=7.9 Hz, 1H), 7.47 (t, J=7.9 Hz, 1H), 7.80 (d, J=7.9 Hz, 1H), 7.87 (s, 1H), 7.98 (dd, J=7.7, 1.7 Hz, 1H), 8.20 (d, J=5.0 Hz, 1H), 8.55 (m, 2H)

The chemical structures of the compound of the present invention are shown in Table 1-6. In the table, the numbers described in the column of R$^3$ show the substitutional site of R$^3$ on the pyrimidine ring.

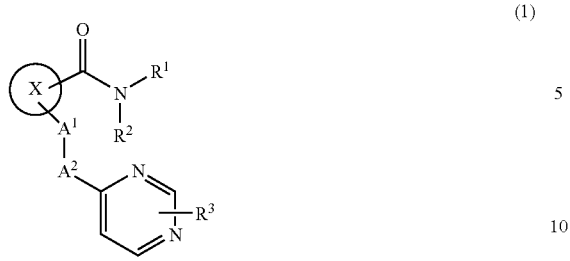
(1)
TABLE 1
| Compd. | X | A¹ | A² | R¹ | R² | R³ |
|---|---|---|---|---|---|---|
| 1-1 | nicotinoyl | S | —CH₂— | 3,5-dimethylphenyl | H | 2-NH₂ |
| 1-2 | nicotinoyl | S | —CH₂— | 4-chlorophenyl | H | 2-NH₂ |
| 1-3 | nicotinoyl | S | —CH₂— | 4-OCF₃-phenyl | H | 2-NH₂ |
| 1-4 | nicotinoyl | S | —CH₂— | indanyl | H | 2-NH₂ |
| 1-5 | nicotinoyl | S | —CH₂— | 3-methylphenyl | H | 2-NH₂ |
| 1-6 | nicotinoyl | S | —CH₂— | 4-tert-butylphenyl | H | 2-NH₂ |
| 1-7 | nicotinoyl | S | —CH₂— | 3-isopropylphenyl | H | 2-NH₂ |

TABLE 1-continued

| Compd. | X (structure) | A¹ | A² | R¹ | R² | R³ |
|---|---|---|---|---|---|---|
| 1-8 | nicotinamide | S | —CH$_2$— | 2,5-dimethoxy-4-chlorophenyl | H | 2-NH$_2$ |
| 1-9 | nicotinamide | S | —CH$_2$— | 4-methoxyphenyl | H | 2-NH$_2$ |
| 1-10 | nicotinamide | S | —CH$_2$— | 4-methoxyphenethyl | H | 2-NH$_2$ |
| 1-11 | nicotinamide | S | —CH$_2$— | quinolin-6-yl | H | 2-NH$_2$ |

TABLE 2

| Compd. | X (structure) | A¹ | A² | R¹ | R² | R³ |
|---|---|---|---|---|---|---|
| 1-12 | nicotinamide | S | —CH$_2$— | isoquinolin-3-yl | H | 2-NH$_2$ |
| 1-13 | nicotinamide | S | —CH$_2$— | morpholin-4-yl | | 2-NH$_2$ |
| 1-14 | nicotinamide | S | —CH$_2$— | 1H-indazol-6-yl | H | 2-NH$_2$ |

TABLE 2-continued

| Compd. | X | A¹ | A² | R¹ | R² | R³ |
|---|---|---|---|---|---|---|
| 1-15 | nicotinamide | S | —CH$_2$— | 4-ethylphenyl | H | 2-NH$_2$ |
| 1-16 | benzamide | S | —CH$_2$— | 3,5-dimethylphenyl | H | 2-NH$_2$ |
| 1-17 | benzamide | S | —CH$_2$— | 4-chlorophenyl | H | 2-NH$_2$ |
| 1-18 | benzamide | S | —CH$_2$— | morpholino | | 2-NH$_2$ |
| 1-19 | benzamide | S | —CH$_2$— | 4-methoxyphenethyl | H | 2-NH$_2$ |
| 1-20 | thiophene-2-carboxamide | S | —CH$_2$— | 3,5-dimethylphenyl | H | 2-NH$_2$ |
| 1-21 | thiophene-2-carboxamide | S | —CH$_2$— | morpholino | | 2-NH$_2$ |
| 1-22 | nicotinamide | S | —CH$_2$— | 3,5-dimethylphenyl | H | H |
| 1-23 | nicotinamide | S | —CH$_2$— | 4-chlorophenyl | H | H |

TABLE 2-continued

| Compd. | X | A¹ | A² | R¹ | R² | R³ |
|---|---|---|---|---|---|---|
| 1-24 | nicotinamide | S | —CH₂— | indanyl | H | H |
| 1-25 | nicotinamide | S | —CH₂— | 4-tert-butylphenyl | H | H |

TABLE 3

| Compd. | X | A¹ | A² | R¹ | R² | R³ |
|---|---|---|---|---|---|---|
| 1-26 | nicotinamide | S | —CH₂— | 3,5-dimethylphenyl | H | 2-SMe |
| 1-27 | nicotinamide | S | —CH₂— | 3,5-dimethylphenyl | H | 2-S(O)Me |
| 1-28 | nicotinamide | S | —CH₂— | 4-chlorophenyl | H | 2-S(O)Me |
| 1-29 | nicotinamide | S | —CH₂— | 4-OCF₃-phenyl | H | 2-S(O)Me |
| 1-30 | nicotinamide | S | —CH₂— | isoquinolinyl | H | 2-S(O)Me |

TABLE 3-continued

| Compd. | X | A¹ | A² | R¹ | R² | R³ |
|---|---|---|---|---|---|---|
| 1-31 | nicotinoyl | S | —CH$_2$— | 3-Cl-phenyl | H | 2-S(O)Me |
| 1-32 | nicotinoyl | S | —CH$_2$— | 3-CF$_3$-phenyl | H | 2-S(O)Me |
| 1-33 | nicotinoyl | S | —CH$_2$— | 3,5-diMe-phenyl | H | 2-NHMe |
| 1-34 | nicotinoyl | S | —CH$_2$— | 3,5-diMe-phenyl | H | 2-NMe$_2$ |
| 2-1 | nicotinoyl | S | —CH$_2$— | 3,5-diMe-phenyl | H | 2-NHAc |
| 2-2 | nicotinoyl | S | —CH$_2$— | 4-Cl-phenyl | H | 2-NHAc |
| 2-3 | nicotinoyl | S | —CH$_2$— | 4-OCF$_3$-phenyl | H | 2-NHAc |
| 2-4 | nicotinoyl | S | —CH$_2$— | indanyl | H | 2-NHAc |
| 3-1 | nicotinoyl | S | —CH$_2$— | 3,5-diMe-phenyl | H | 2-NAc$_2$ |

TABLE 3-continued

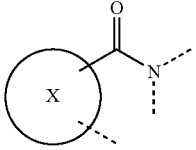

| Compd. | | A¹ | A² | R¹ | R² | R³ |
|---|---|---|---|---|---|---|

TABLE 4

| Compd. | X | A¹ | A² | R¹ | R² | R³ |
|---|---|---|---|---|---|---|
| 3-2 | pyridine-3-carboxamide | S | —CH₂— | indanyl | H | 2-NAc2 |
| 4-1 | pyridine-3-carboxamide | S | —CH₂— | 3,5-dimethylphenyl | H | N-cyclopropylamino, 2 |
| 4-2 | pyridine-3-carboxamide | S | —CH₂— | 4-chlorophenyl | H | morpholino, 2 |
| 4-3 | pyridine-3-carboxamide | S | —CH₂— | 4-OCF₃-phenyl | H | morpholino, 2 |
| 4-4 | pyridine-3-carboxamide | S | —CH₂— | 3,5-dimethylphenyl | H | morpholino, 2 |
| 4-5 | pyridine-3-carboxamide | S | —CH₂— | 4-chlorophenyl | H | N-cyclopropylamino, 2 |
| 4-6 | pyridine-3-carboxamide | S | —CH₂— | 4-OCF₃-phenyl | H | N-cyclopropylamino, 2 |

TABLE 4-continued

| Compd. | (X ring with C(O)N structure) | A¹ | A² | R¹ | R² | R³ |
|---|---|---|---|---|---|---|
| 4-7 | pyridine-3-carboxamide | S | —CH₂— | isoquinolin-3-yl | H | 2-NHcyclopropyl |
| 4-8 | pyridine-3-carboxamide | S | —CH₂— | 3-Cl-phenyl | H | 2-NHcyclopropyl |
| 4-9 | pyridine-3-carboxamide | S | —CH₂— | 3-CF₃-phenyl | H | 2-NHcyclopropyl |
| 4-10 | pyridine-3-carboxamide | S | —CH₂— | 3,5-dimethylphenyl | H | 2-NHBu-n |
| 4-11 | pyridine-3-carboxamide | S | —CH₂— | 4-Cl-phenyl | H | 2-NHBu-n |
| 4-12 | pyridine-3-carboxamide | S | —CH₂— | 4-OCF₃-phenyl | H | 2-NHBu-n |
| 4-13 | pyridine-3-carboxamide | S | —CH₂— | isoquinolin-3-yl | H | 2-NHcyclobutyl |

TABLE 5

| Compd. | (X ring with C(O)N) | A¹ | A² | R¹ | R² | R³ |
|---|---|---|---|---|---|---|
| 4-14 | pyridine-3-carboxamide | S | —CH₂— | 3-Cl-phenyl | H | —NH-cyclobutyl (2) |
| 4-15 | pyridine-3-carboxamide | S | —CH₂— | 3,5-dimethylphenyl | H | 4-acetylpiperazin-1-yl (2) |
| 4-16 | pyridine-3-carboxamide | S | —CH₂— | 4-Cl-phenyl | H | 4-acetylpiperazin-1-yl (2) |
| 4-17 | pyridine-3-carboxamide | S | —CH₂— | 4-OCF₃-phenyl | H | 4-acetylpiperazin-1-yl (2) |
| 4-18 | pyridine-3-carboxamide | S | —CH₂— | 3,5-dimethylphenyl | H | —NH-CH(CH₃)-phenyl (2) |
| 4-19 | pyridine-3-carboxamide | S | —CH₂— | 3,5-dimethylphenyl | H | —NH-CH₂CH₂-OH (2) |
| 4-20 | pyridine-3-carboxamide | S | —CH₂— | 3,5-dimethylphenyl | H | —NH-CH₂CH₂-O-CH₂CH₃ (2) |
| 4-21 | pyridine-3-carboxamide | S | —CH₂— | 4-OCF₃-phenyl | H | —NH-CH₂CH₂-morpholin-4-yl (2) ·HCl |

TABLE 5-continued

| Compd. | X | A¹ | A² | R¹ | R² | R³ |
|---|---|---|---|---|---|---|
| 4-22 | nicotinamide | S | —CH₂— | 3,5-dimethylphenyl | H | —NH-CH₂CH₂-O-ethyl (2) |
| 4-23 | nicotinamide | S | —CH₂— | 4-chlorophenyl | H | —NH-CH₂CH₂-morpholine (2) |
| 4-24 | nicotinamide | S | —CH₂— | 3,5-dimethylphenyl | H | —NH-(4-hydroxycyclohexyl) (2) |

TABLE 6

| Compd. | X | A¹ | A² | R¹ | R² | R³ |
|---|---|---|---|---|---|---|
| 4-25 | nicotinamide | S | —CH₂— | 3,5-dimethylphenyl | H | 4-(2-hydroxyethyl)piperazin-1-yl (2) |
| 4-26 | nicotinamide | S | —CH₂— | isoquinolin-3-yl | H | 4-(2-hydroxyethyl)piperazin-1-yl (2) |
| 4-27 | nicotinamide | S | —CH₂— | 3-chlorophenyl | H | 4-(2-hydroxyethyl)piperazin-1-yl (2) |
| 4-28 | nicotinamide | S | —CH₂— | 3-trifluoromethylphenyl | H | 4-(2-hydroxyethyl)piperazin-1-yl (2) |
| 4-29 | nicotinamide | S | —CH₂— | 3,5-dimethylphenyl | H | 4-methylpiperazin-1-yl (2) |

TABLE 6-continued

[Structures for entries 4-30 through 4-36, each showing a nicotinamide group (O=C-N with pyridine) in column 1, "S" in column 2, —CH₂— linker in column 3, various aryl/heteroaryl groups in column 4, H in column 5, and piperazine derivatives with "2" in column 6]

| No. | | | | | | |
|---|---|---|---|---|---|---|
| 4-30 | nicotinamide | S | —CH₂— | isoquinolin-3-yl | H | 4-methylpiperazin-1-yl, 2 |
| 4-31 | nicotinamide | S | —CH₂— | 3-chlorophenyl | H | 4-methylpiperazin-1-yl, 2 |
| 4-32 | nicotinamide | S | —CH₂— | 3-(trifluoromethyl)phenyl | H | 4-methylpiperazin-1-yl, 2 ·HCl |
| 4-33 | nicotinamide | S | —CH₂— | 3,5-dimethylphenyl | H | piperazin-1-yl (NH), 2 |
| 4-34 | nicotinamide | S | —CH₂— | isoquinolin-3-yl | H | piperazin-1-yl (NH), 2 |
| 4-35 | nicotinamide | S | —CH₂— | 3-chlorophenyl | H | piperazin-1-yl (NH), 2 |
| 4-36 | nicotinamide | S | —CH₂— | 3-(trifluoromethyl)phenyl | H | piperazin-1-yl (NH), 2 |

PREPARATION EXAMPLES

Hereinafter, typical preparation examples of the compound of the present invention are shown.

1) Tablet (in 100 mg)

| | |
|---|---|
| Compound of the present invention | 1 mg |
| Lactose | 66.4 mg |
| Cornstarch | 20 mg |
| Calcium carboxymethyl cellulose | 6 mg |
| Hydroxypropyl cellulose | 4 mg |
| Magnesium stearate | 0.6 mg |

The tablet of the above-mentioned formulation is coated using 2 mg of a coating agent (for example, a conventional coating agent such as hydroxypropylmethyl cellulose, macrogol or a silicone resin), whereby a desired coated tablet is obtained. In addition, a desired tablet can be obtained by appropriately changing the kinds and amounts of the compound of the present invention and additives.

2) Capsule

| Formulation 2 (in 150 mg) | |
|---|---|
| Compound of the present invention | 5 mg |
| Lactose | 145 mg |

A desired capsule can be obtained by appropriately changing the mixing ratio of the compound of the present invention to lactose.

3) Eye Drop

| Formulation 3 (in 100 mL) | |
|---|---|
| Compound of the present invention | 100 mg |
| Sodium chloride | 900 mg |
| Polysorbate 80 | 200 mg |
| Sodium hydroxide | q.s. |
| Hydrochloric acid | q.s. |
| Sterile purified water | q.s. |

A desired eye drop can be obtained by appropriately changing the kinds and the amounts of the compound of the present invention and additives.

[Pharmacological Tests]

1. Evaluation Test for Antiangiogenic Effect

As one of the widely used methods of evaluating antiangiogenic effects of drugs, a cell proliferation inhibitory action test using a VEGF-induced HUVEC proliferation reaction evaluation system has been reported in Cancer Res., 59, 99-106 (1999). According to the method described in the above-mentioned document, a cell proliferation inhibitory action test of the compound of the present invention was carried out, and the cell proliferation inhibition rate was calculated. Then, the antiangiogenic effect of each of the compound of the present invention was evaluated using the obtained rate as an index.

(Preparation of Test Compound Solution)

Each test compound was dissolved in dimethyl sulfoxide (hereinafter abbreviated as DMSO), and the obtained solution was diluted with a commercially available phosphate buffer solution (hereinafter abbreviated as PBS), whereby a 20 µg/mL test compound solution was prepared.

(Preparation of HUVEC Suspension)

HUVEC was suspended in F12K medium containing 0.5% fetal bovine serum (hereinafter abbreviated as FBS), whereby a $2 \times 10^4$ cells/mL HUVEC suspension was prepared.

(Preparation of VEGF Solution)

VEGF was dissolved in PBS containing 0.1% bovine serum albumin, and the obtained solution was diluted with F12K medium containing 0.5% FBS, whereby a 400 ng/mL VEGF solution was prepared.

(Test Method and Measurement Method)

1) The HUVEC suspension was inoculated in an amount of 100 µL into each well of a 96-well plate coated with type I collagen ($2 \times 10^3$ cells per well).

2) One day after the inoculation, the test compound solution was added in an amount of 5 µL per well.

3) One hour after the addition of the test compound solution, the VEGF solution was added in an amount of 5 µL per well.

4) Three days after the addition of the VEGF solution, WST-8 assay reagent (Dojin Chemical Co., Ltd.) was added in an amount of 10 µL per well.

5) After 3 hours, the above-mentioned plate was attached to an absorptiometer (Multilabel Counter ARVO), and an absorbance at 450 nm of suspension in each well (hereinafter referred to as a test compound suspension) was measured.

6) A test was carried out in the same manner as in the above 1) to 5) except that 1.0% DMSO was used instead of the test compound solution. The result was used as a control.

Incubation was carried out under conditions of 37° C., 5% carbon dioxide and 95% oxygen in an incubator throughout the above-mentioned test steps.

(Calculation of Cell Proliferation Inhibition Rate)

The cell proliferation inhibition rate (%), which was used as an index of an antiangiogenic effect, was calculated using the following calculation equation.

Cell proliferation inhibition rate (%)=100−{(Absorbance of test compound suspension−A)/(absorbance of control−A)}×100  (Calculation Equation)

A: Absorbance of only cell suspension (cells+medium)

(Test Results and Discussion)

As an example of the test results, the cell proliferation inhibition rates (%) of the test compounds (Compound 1-1, Compound 1-7, Compound 1-12, Compound 1-16, Compound 1-20, Compound 1-22, Compound 1-26, Compound 1-33, Compound 2-1, Compound 2-2, Compound 2-4, Compound 3-1, Compound 4-1, Compound 4-4, Compound 4-6, Compound 4-9, Compound 4-19, Compound 4-22, Compound 4-25 and Compound 4-36 are shown in Table 7.

TABLE 7

| Compound | Cell proliferation inhibition rate (%) |
|---|---|
| 1-1 | 96 |
| 1-7 | 96 |
| 1-12 | 84 |
| 1-16 | 100 |
| 1-20 | 100 |
| 1-22 | 100 |
| 1-26 | 100 |
| 1-33 | 100 |
| 2-1 | 100 |
| 2-2 | 97 |
| 2-4 | 99 |
| 3-1 | 100 |
| 4-1 | 100 |
| 4-4 | 100 |
| 4-6 | 100 |
| 4-9 | 100 |
| 4-19 | 100 |
| 4-22 | 100 |
| 4-25 | 100 |
| 4-36 | 100 |

As shown in Table 7, the compound of the present invention exhibited an excellent cell proliferation inhibitory action. Accordingly, the compound of the present invention has an excellent antiangiogenic effect.

The invention claimed is:

1. A compound represented by the following general formula (1) or a salt thereof:

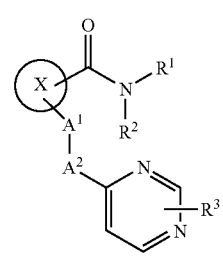

wherein the ring X represents

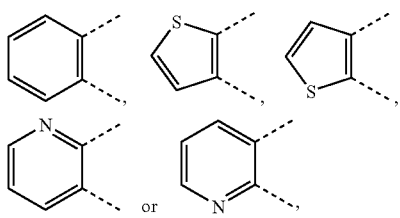

which may have one or plural substituents selected from a halogen atom and an alkyl group;

$R^1$ and $R^2$ may be the same or different and each represents a hydrogen atom, an alkyl group, an aryl group or an aromatic heterocyclic group;

in the case where $R^1$ or $R^2$ is an alkyl group, the alkyl group may have one or plural substituents selected from an aryl group, a halogenoaryl group, an alkoxyaryl group and an alkylaryl group;

in the case where $R^1$ or $R^2$ is an aryl group, the aryl group may have one or plural substituents selected from a halogen atom, a hydroxy group, an alkoxy group, a halogenoalkoxy group, an alkyl group, a halogenoalkyl group, an aryl group, a halogenoaryl group, an alkoxyaryl group and an alkylaryl group;

$R^1$ and $R^2$ may be combined together to form a nonaromatic heterocycle;

$R^3$ represents a hydrogen atom, a halogen atom, a hydroxy group, an alkoxy group, an aryloxy group, an alkyl group, an aryl group, an amino group, an alkylamino group, a cycloalkylamino group, an arylamino group, an alkylcarbonylamino group, an arylcarbonylamino group, a mercapto group, an alkylthio group, an arylthio group, an alkylsulfinyl group or a nonaromatic heterocyclic group;

in the case where $R^3$ is an alkylamino group or an alkylcarbonylamino group, the alkyl moiety of which may have one or plural substituents selected from a hydroxy group, an alkoxy group, an aryl group, an amino group, an alkylamino group and a nonaromatic heterocyclic group;

in the case where $R^3$ is a cycloalkylamino group, the cycloalkyl moiety of which may have one or plural substituents selected from a hydroxy group and an alkoxy group;

in the case where $R^3$ is a nonaromatic heterocyclic group, the ring of which may have one or plural substituents selected from an alkyl group, a hydroxyalkyl group and an alkoxyalkyl group;

$A^1$ represents a sulfur atom, a sulfinyl group or a sulfonyl group; and $A^2$ represents an alkylene group.

2. The compound or a salt thereof according to claim 1, wherein in the general formula (1), the ring X represents:

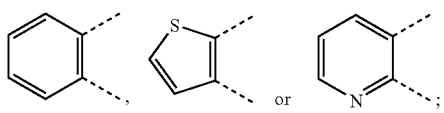

$R^1$ represents an aryl group or an aromatic heterocyclic group;

in the case where $R^1$ is an aryl group, the aryl group may have one or plural substituents selected from a halogen atom, a hydroxy group, an alkoxy group, a halogenoalkoxy group, an alkyl group, a halogenoalkyl group and an aryl group;

$R^2$ represents a hydrogen atom;

$R^3$ represents a hydrogen atom, an amino group, an alkylamino group, a cycloalkylamino group, an arylamino group, an alkylcarbonylamino group, a mercapto group, an alkylthio group, an arylthio group, an alkylsulfinyl group or a nonaromatic heterocyclic group;

in the case where $R^3$ is an alkylamino group, the alkyl moiety of which may have one or plural substituents selected from a hydroxy group, an alkoxy group, an aryl group and a nonaromatic heterocyclic group;

in the case where $R^3$ is a cycloalkylamino group, the cycloalkyl moiety of which may have one or plural substituents selected from a hydroxy group and an alkoxy group;

in the case where $R^3$ is a nonaromatic heterocyclic group, the ring of which may have one or plural substituents selected from an alkyl group, a hydroxyalkyl group and an alkoxyalkyl group;

$A^1$ represents a sulfur atom; and $A^2$ represents an alkylene group.

3. The compound or a salt thereof according to claim 1, wherein in the general formula (1), the ring X represents:

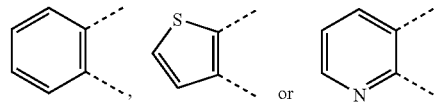

$R^1$ represents an aryl group or an aromatic heterocyclic group;

in the case where $R^1$ is an aryl group, the aryl group may have one or plural substituents selected from a halogen atom, an alkoxy group, a halogenoalkoxy group, an alkyl group and a halogenoalkyl group;

$R^2$ represents a hydrogen atom;

$R^3$ represents a hydrogen atom, an amino group, an alkylamino group, a cycloalkylamino group, an alkylcarbonylamino group, an alkylthio group, or a nonaromatic heterocyclic group;

in the case where $R^3$ is an alkylamino group, the alkyl moiety of which may have one or plural substituents selected from a hydroxy group, an alkoxy group, an aryl group and a nonaromatic heterocyclic group;

in the case where $R^3$ is a cycloalkylamino group, the cycloalkyl moiety of which may have one or plural hydroxy groups as substituents;

in the case where $R^3$ is a nonaromatic heterocyclic group, the ring of which may have one or plural substituents selected from an alkyl group and a hydroxyalkyl group;

$A^1$ represents a sulfur atom; and $A^1$ represents an alkylene group.

4. The compound or a salt thereof according to claim 1, wherein in the general formula (1),
the ring X represents:

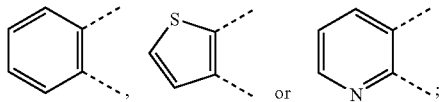

R¹ represents a phenyl group, a 3-chlorophenyl group, a 4-chlorophenyl group, a 4-methoxyphenyl group, a 4-trifluoromethoxyphenyl group, a 4-n-propylphenyl group, a 3-isopropylphenyl group, a 4-tert-butylphenyl group, a 3-trifluoromethylphenyl group, a 5-chloro-2,4-dimethoxyphenyl group, a 3,5-dimethylphenyl group, an indan-5-yl group, a 1H-indazol-6-yl group, a quinolin-6-yl group or an isoquinolin-3-yl group;
R² represents a hydrogen atom;
R³ represents a hydrogen atom, an amino group, a methylamino group, an n-butylamino group, a dimethylamino group, a 2-hydroxyethylamino group, a 2-ethoxyethylamino group, a 1-phenylethylamino group, a 2-morpholinoethylamino group, a cyclopropylamino group, a cyclobutylamino group, a 4-hydroxycyclohexylamino group, an acetylamino group, a diacetylamino group, a methylthio group, a morpholino group, a piperazinyl group, a 4-methylpiperazinyl group or a 4-(2-hydroxyethyl)piperazinyl group;
A¹ represents a sulfur atom; and
A² represents a methylene group.

5. A compound selected from the group consisting of
2-(2-Aminopyrimidin-4-ylmethylthio)-N-(3,5-dimethylphenyl)pyridine-3-carboxamide,
2-(2-Aminopyrimidin-4-ylmethylthio)-N-(4-chlorophenyl)pyridine-3-carboxamide,
2-(2-Aminopyrimidin-4-ylmethylthio)-N-(4-trifluoromethoxyphenyl)pyridine-3-carboxamide,
2-(2-Aminopyrimidin-4-ylmethylthio)-N-(3-isopropylphenyl)pyridine-3-carboxamide,
2-(2-Aminopyrimidin-4-ylmethylthio)-N-(quinolin-6-yl)pyridine-3-carboxamide,
2-(2-Aminopyrimidin-4-ylmethylthio)-N-(isoquinolin-3-yl)pyridine-3-carboxamide,
2-(2-Aminopyrimidin-4-ylmethylthio)-N-(3,5-dimethylphenyl)benzamide,
2-(2-Aminopyrimidin-4-ylmethylthio)-N-(4-chlorophenyl)benzamide,
3-(2-Aminopyrimidin-4-ylmethylthio)-N-(3,5-dimethylphenyl)thiophene-2-carboxamide,
N-(3,5-Dimethylphenyl)-2-(pyrimidin-4-ylmethylthio)pyridine-3-carboxamide,
N-(4-Chlorophenyl)-2-(pyrimidin-4-ylmethylthio)pyridine-3-carboxamide,
N-(3,5-Dimethylphenyl)-2-(2-methylthiopyrimidin-4-ylmethylthio)pyridine-3-carboxamide
N-(3,5-Dimethylphenyl)-2-(2-methylaminopyrimidin-4-ylmethylthio)pyridine-3-carboxamide,
2-(2-Dimethylaminopyrimidin-4-ylmethylthio)-N-(3,5-dimethylphenyl)pyridine-3-carboxamide,
2-(2-Acetylaminopyrimidin-4-ylmethylthio)-N-(3,5-dimethylphenyl)pyridine-3-carboxamide,
2-(2-Acetylaminopyrimidin-4-ylmethylthio)-N-(4-chlorophenyl)pyridine-3-carboxamide,
2-(2-Acetylaminopyrimidin-4-ylmethylthio)-N-(4-trifluoromethoxyphenyl)pyridine-3-carboxamide,
2-(2-Acetylaminopyrimidin-4-ylmethylthio)-N-(indan-5-yl)pyridine-3-carboxamide,
2-(2-Diacetylaminopyrimidin-4-ylmethylthio)-N-(3,5-dimethylphenyl)pyridine-3-carboxamide,
2-(2-Cyclopropylaminopyrimidin-4-ylmethylthio)-N-(3,5-dimethylphenyl)pyridine-3-carboxamide,
N-(4-Chlorophenyl)-2-(2-morpholinopyrimidin-4-ylmethylthio)pyridine-3-carboxamide,
2-(2-Morpholinopyrimidin-4-ylmethylthio)-N-(4-trifluoromethoxyphenyl)pyridine-3-carboxamide,
N-(3,5-Dimethylphenyl)-2-(2-morpholinopyrimidin-4-ylmethylthio)pyridine-3-carboxamide,
N-(4-Chlorophenyl)-2-(2-cyclopropylaminopyrimidin-4-ylmethylthio)pyridine-3-carboxamide,
2-(2-Cyclopropylaminopyrimidin-4-ylmethylthio)-N-(4-trifluoromethoxyphenyl)pyridine-3-carboxamide,
2-(2-Cyclopropylaminopyrimidin-4-ylmethylthio)-N-(3-trifluoromethylphenyl)pyridine-3-carboxamide,
2-(2-n-Butylaminopyrimidin-4-ylmethylthio)-N-(3,5-dimethylphenyl)pyridine-3-carboxamide,
2-[2-(4-Acetylpiperazin-1-yl)pyrimidin-4-ylmethylthio]-N-(3,5-dimethylphenyl)pyridine-3-carboxamide,
N-(3,5-Dimethylphenyl)-2-[2-(2-hydroxyethyl)aminopyrimidin-4-ylmethylthio]pyridine-3-carboxamide,
2-[2-(2-Ethoxyethyl) aminopyrimidin-4-ylmethylthio]-N-(4-trifluoromethoxyphenyl)pyridine-3-carboxamide,
N-(4-Chlorophenyl)-2-(pyrimidin-4-ylmethylthio)pyridine-3-carboxamide,
N-(3,5-Dimethylphenyl)-2-[2-(4-(2-hydroxyethyl)piperazin-1-yl)pyrimidin-4-ylmethylthio]pyridine-3-carboxamide,
N-(3,5-Dimethylphenyl)-2-[2-(4-methylpiperazin-1-yl)pyrimidin-4-ylmethylthio]pyridine-3-carboxamide and
2-[2-(piperazin-1-yl)pyrimidin-4-ylmethylthio]-N-(3-trifluorophenyl)pyridine-3-carboxamide, or a salt thereof.

6. A pharmaceutical composition comprising the compound or a salt thereof according to claim 1 and a pharmaceutically acceptable carrier.

* * * * *